(12) United States Patent
Bose et al.

(10) Patent No.: US 10,114,027 B2
(45) Date of Patent: Oct. 30, 2018

(54) BETA-GLUCAN ASSAY METHODS

(71) Applicant: Biothera, Inc., Eagan, MN (US)

(72) Inventors: Nandita Bose, Plymouth, MN (US); Mary A. Antonysamy, Woodbury, MN (US); Keith B. Gorden, Woodbury, MN (US); Richard Walsh, Lino Lakes, MN (US); Michael E. Danielson, St. Paul, MN (US); Peter Maimonis, Westwood, MA (US)

(73) Assignee: Biothera, Inc., Eagan, MN (US)

( * ) Notice: Subject to any disclaimer, the term of this patent is extended or adjusted under 35 U.S.C. 154(b) by 0 days.

(21) Appl. No.: 15/845,421

(22) Filed: Dec. 18, 2017

(65) Prior Publication Data

US 2018/0128836 A1  May 10, 2018

Related U.S. Application Data

(63) Continuation of application No. 15/101,065, filed as application No. PCT/US2014/067944 on Dec. 1, 2014, now Pat. No. 9,885,726.

(60) Provisional application No. 62/005,335, filed on May 30, 2014, provisional application No. 61/912,275, filed on Dec. 5, 2013.

(51) Int. Cl.
| | |
|---|---|
| *G01N 33/53* | (2006.01) |
| *G01N 33/68* | (2006.01) |
| *C07K 16/14* | (2006.01) |
| *G01N 33/569* | (2006.01) |
| *A61K 39/00* | (2006.01) |
| *C07K 16/16* | (2006.01) |

(52) U.S. Cl.
CPC ..... *G01N 33/6854* (2013.01); *A61K 39/0002* (2013.01); *C07K 16/14* (2013.01); *G01N 33/53* (2013.01); *G01N 33/56961* (2013.01); *C07K 16/16* (2013.01); *G01N 2400/24* (2013.01); *G01N 2800/24* (2013.01)

(58) Field of Classification Search
None
See application file for complete search history.

(56) References Cited

U.S. PATENT DOCUMENTS

| 6,294,321 | B1 | 9/2001 | Wakshull et al. |
| 7,981,447 | B2 | 7/2011 | Cox |
| 8,822,163 | B2 | 9/2014 | Yoneda |
| 2008/0103112 | A1 | 5/2008 | Magee et al. |
| 2015/0125461 | A1 | 5/2015 | Grossman |

FOREIGN PATENT DOCUMENTS

| AU | 2013 203 785 A1 | 5/2013 |
| CN | 102119332 A | 7/2011 |
| CN | 102356317 A | 2/2012 |
| CN | 102866255 A | 1/2013 |
| CN | 103235116 A | 8/2013 |
| JP | 2008164579 A | 7/2008 |
| JP | 2008273916 A | 11/2008 |
| JP | 2010187634 A | 9/2010 |
| WO | WO 2004/036222 A1 | 4/2004 |
| WO | WO 2009/134891 A2 | 11/2009 |
| WO | WO 2011/044234 A2 | 4/2011 |
| WO | WO 2012/154680 A1 | 11/2012 |
| WO | WO 2013/114002 A2 | 8/2013 |
| WO | WO 2013/165591 A1 | 11/2013 |

OTHER PUBLICATIONS

International Preliminary Report on Patentability for PCT/US2014/067944, issued by the International Bureau of WIPO dated Jun. 16, 2016; 6 pgs.
International Search Report and Written Opinion for PCT/US2014/067944, issued by the United States Patent and Trademark Office, dated Feb. 26, 2015; 8 pgs.
Antonysamy et al., "A Novel Mechanism for Recognition of a Small Molecule Carbohydrate Immunotherapeutic by Human Myeloid Cells: Potential for Modulation of Efficacy," *Front Immunol.*, 2013, 15th International Congress of Immunology (ICI), Milan, Italy, Aug. 22-27, 2013.
Bose et al., "Binding of soluble yeast β-glucan to human neutrophils and monocytes is complement-dependent", Aug. 12, 2013, *Frontiers in Immunology*, 4(230):1-14.
Bose et al., "Endogenous anti-β-glucan antibodies as a potential predictive biomarker for clinical response to imprime PGG immunotherapy in non-small cell lung cancer (NSCLC) patients", *J Clin Oncol*, May 2014;32(15-Supplement), Abstract: 3 pgs.
Bose et al., "Endogenous anti-β-glucan antibodies as a potential predictive biomarker for clinical response to imprime PGG immunotherapy in non-small cell lung cancer (NSCLC) patients", J Clin Oncol, May 2014;32(15-Supplement), Poster; 1 pgs.
Chan, et al., "Analysing antibody response based on data obtained from serial dilution methods", *Statistics in Medicine*, Oct./Dec. 1983;2(4):447-454.
Chiani et al., "Anti-B-glucan antibodies in healthy human subjects," *Vaccine*, 2009;27:513-519.
"Lung Cancer", NCCN Guidelines for Patents®, National Comprehensive Cancer Network, Fort Washington, PA, Version 1.2016, 130 pgs. Found online [https://www.nccn.org/patients/guidelines/lung-nsclc/files/assets/common/downloads/files/nsclc.pdf].
Hsu et al., "Complement activation mediates cetuximab inhibition of non-small cell lung cancer tumor growth in vivo," *Molecular Cancer*, 2010;9:139: 8 pgs.

(Continued)

*Primary Examiner* — Changhwa J Cheu
(74) *Attorney, Agent, or Firm* — Mueting, Raasch & Gebhardt, P.A.

(57) ABSTRACT

This disclosure provides, in one aspect, a method for analyzing a sample from a subject for a biomarker that is indicative of the subject's immune response to β-glucan. Generally, the method includes obtaining a biological sample from a subject, analyzing the sample for a biomarker anti-β-glucan antibody compared to a reference standard, computing a Relative Antibody Unit (RAU) value for anti-β-glucan antibody in the sample, and identifying the subject as biomarker positive if the RAU value is greater than a predetermined RAU value for the biomarker anti-β-glucan antibody.

19 Claims, 25 Drawing Sheets

(56) References Cited

OTHER PUBLICATIONS

Ishibashi et al., "Characterization of Blood ([beta]-1,3-glucan and Anti-([beta]-glucan Antibody in Hemodialysis Patients Using Culinary-Medicinal Royal Sun Agaricus," *Int Journal of Medicinal Mushrooms*, Jan. 1, 2011;13(2):101-107.
Ishibashi et al., "Analysis of the Titer and Reactivity of Antibody/ies Against Fungal Cell Wall [beta]-Glucans in Human Sera," *Int Journal of Medicinal Mushrooms*, Jan. 1, 2013;15(2):115-126.
Ishibashi et al., "Effect of Oral Administration of Dried Royal Sun Agaricus, *Agaricus brasiliensis* S. Wasser et al. (Agaricomycetideae), Fruit Bodies on Anti-beta-Glucan Antibody Titers in Humans," *Int Journal of Medicinal Mushrooms*, Jan. 1, 2009;11(2):117-131.
Immunology 2013, The American Associate of Immunologists, Honolulu, Hawaii; Annual Meeting; May 3-7, 2013, found online at <http://www.immunology2013.org/>.
"Cancer Immunology and Immunotherapy (J4)," Summary of Meeting; Keystone Symposia on Molecular and Cellular Biology, Cancer Immunology and Immunotherapy Conference 2013, Vancouver, Canada; Jan. 27-Feb. 1, 2013, Organizers Dranoff, Glenn; June, Carl H.; Topalian, Suzanne L., Abstract (1 pg.); found on line at <http://www.keystonesymposia.org/index.cfm?e=Web.Meeting.Program&Meeting id=1197>.
Leonardi et al., "Determination of Anti-Beta Glucan Immunoglobulin G by Means of the Eliza Enzyme Linked Immunosorbent Assay Method," *Bulletin de La Societe Francaise de Mycologie Medicale*, 1984;13(1):177-182. English Translation Included.
Li et al., "Yeast β-Glucan Amplifies Phagocyte Killing of iC3b-Opsonized Tumor Cells via Complement Receptor 3-Syk-Phosphatidylinositol 3-Kinase Pathway", *Journal of Immunology*, 2006;177:1661-1669.
Li et al., "Combined Yeast β-Glucan and Antitumor Monoclonal Antibody Therapy Requires C5a-Mediated Neutrophil Chemotaxis via Regulation of Decay-Accelerating Factor CD55", *Cancer Research*, Aug. 1, 2007;67:7421-7430.
Liu et al., "Combined yeast-derived β-glucan with anti-tumor monoclonal antibody for cancer immunotherapy," J Exp. Mol. Pathol., Jun. 2009;86(3):208-2014.
Lynch et al., "Cetuximab and First-Line Taxane/Carboplatin Chemotherapy in Advanced Non-Small-Cell Lung Cancer: Results of the Randomized Multicenter Phase III Trial BMS099,", *J. Clin. Oncol.*, Feb. 2010;28(6):911-917.
Noss et al., "IgG to Various Beta-Glucans in a Human Adult Population," *Int. Arch. Allergy Immunol.*, 2012;157:98-108. First published online Sep. 7, 2011.
Pirker et al., "EGFR expression as a predictor of survival for first-line chemotherapy plus cetuximab in patients with advanced non-small-cell lung cancer: analysis of data from the phase 3 Flex study," *The Lancet Oncology*, Jan. 2012;13(1):33-42.
Qi et al., "Differential pathways regulating innate and adaptive antitumor immune responses by particulate and soluble yeast-derived β-glucans", *Blood*, Jun. 23, 2011;117(25):6825-6836.
"RNA Silencing (C7)," Summary of Meeting; Keystone Symposia on Molecular and Cellular Biology, Cancer Immunology and Immunotherapy Conference 2013, Whistler, British Colombia, Canada; Mar. 19-24, 2013, Organizers Baulcombe, David C; Bozzoni, Irene, Abstract (1 pg.); found on line at <http://www.keystonesymposia.org/13C7>.
Salvador et al., "Yeast-Derived β-Glucan Augments the Therapeutic Efficacy Mediated by Anti-Vascular Endothelial Growth Factor Monoclonal Antibody in Human Carcinoma Xenograft Models", *Cancer Research*, Feb. 15, 2008;14(4):1239-1247.
Zhong et al., "Effect of Yeast-derived β-glucan in Conjunction With Bevacizumab for the Treatment of Human Lung Adenocarcinoma in Subcutaneous and Orthotopic Xenograft Models", Journal of Immunotherapy, Sep. 2009;32(7):703-712.

(A)

(B)

(A)

(B)

BETA-GLUCAN ASSAY METHODS

CROSS-REFERENCE TO RELATED APPLICATION

This application is a continuation of U.S. application Ser. No. 15/101,065, filed 2 Jun. 2016, which is the § 371 U.S. National Stage of International Application No. PCT/US2014/067944, filed 1 Dec. 2014, which claims priority to U.S. Provisional Patent Application Ser. No. 61/912,275, filed Dec. 5, 2013, and U.S. Provisional Patent Application Ser. No. 62/005,335, filed May 30, 2014, each of which is incorporated herein by reference.

SUMMARY

This disclosure provides methods for analyzing a sample from a subject for a biomarker that is indicative of the subject's immune response to β-glucan.

In some embodiments, the method generally includes obtaining a biological sample from a subject, analyzing the sample for a biomarker anti-β-glucan antibody compared to a reference standard, computing an anti-β-glucan antibody concentration or Relative Antibody Unit (RAU) value for anti-β-glucan antibody in the sample, and identifying the subject as biomarker positive if the anti-β-glucan antibody concentration or RAU value is greater than a predetermined anti-β-glucan antibody concentration or RAU value for the biomarker anti-β-glucan antibody.

In other embodiments, the method generally includes obtaining a biological sample from a subject, analyzing the sample for a biomarker anti-β-glucan antibody compared to a reference standard, and identifying the subject as biomarker positive if the sample contains an amount of the anti-β-glucan antibody that is greater than a predetermined cutoff value for the biomarker anti-β-glucan antibody that separates biomarker-positive subjects from biomarker-negative subjects.

In some embodiments, the biomarker anti-β-glucan antibody can be IgG. In some of these embodiments, the predetermined RAU value can be 200.

In some embodiments, the biomarker anti-β-glucan antibody can be IgM. In some of these embodiments, the predetermined RAU value can be 300.

In some embodiments, the method can further include administering to a subject identified as biomarker positive a composition that includes β-glucan.

In some embodiments, the method can further include administering to a subject identified as biomarker positive a composition that includes anti-β-glucan IgG$_2$.

In some embodiments, the β-glucan is derived from yeast such as, for example, a β-1,3/1,6 glucan. In certain embodiments, the β-glucan can include β(1,6)-[poly-(1,3)-D-glucopyranosyl]-poly-β(1,3)-D-glucopyranose.

In some embodiments, analyzing the sample for a biomarker anti-β-glucan antibody can involve using an enzyme-linked immunosorbent assay (ELISA).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1A:
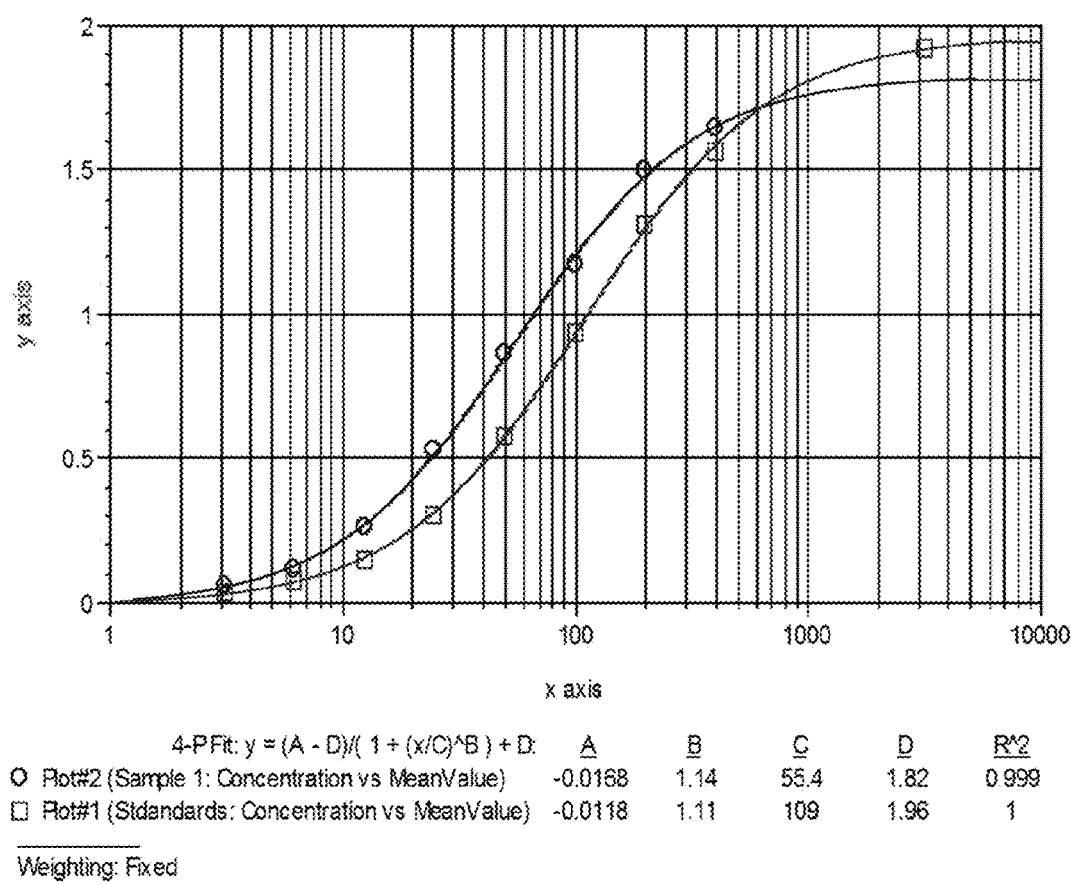
FIG. 1A. An arbitrary value of 160 was assigned to the reference serum (i.e., 160 Relative Antibody Units [RAU]/mL). Thus, the highest point on the calibration curve, the 1:400 dilution, results in a value of 400 mRAU/mL and at the lowest point on the calibration curve, the 1:51200 dilution, results in a value of 3.125 mRAU/mL). Mean RAU/mL=365.

β-glucans are polymers of glucose derived from a variety of microbiological and plant sources including, for example, yeast, bacteria, algae, seaweed, mushroom, oats, and barley. Of these, yeast β-glucans have been extensively evaluated for their immunomodulatory properties. Yeast β-glucans can be present as various forms such as, for example, intact yeast, zymosan, purified whole glucan particles, solubilized zymosan polysaccharide, or highly-purified soluble β-glucans of different molecular weights. Structurally, yeast β-glucans are composed of glucose monomers organized as a β-(1,3)-linked glucopyranose backbone with periodic β-(1, 3) glucopyranose branches linked to the backbone via β-(1, 6) glycosidic linkages. The different forms of yeast β-glucans can function differently from one another. The mechanism through which yeast β-glucans exert their immunomodulatory effects can be influenced by the structural differences between different forms of the β-glucans such as, for example, its particulate or soluble nature, tertiary conformation, length of the main chain, length of the side chain, and frequency of the side chains. The immune stimulating functions of yeast β-glucans are also dependent upon the receptors engaged in different cell types in different species, which again, can be dependent on the structural properties of the β-glucans.

In general, β-glucan immunotherapies can include administering to a subject any suitable form of β-glucan or any combination of two or more forms of β-glucan. Suitable β-glucans and the preparation of suitable β-glucans from their natural sources are described in, for example, U.S. Patent Application Publication No. US2008/0103112 A1. In some cases, the β-glucan may be derived from a yeast such as, for example, Saccharomyces cerevisiae. In certain cases, the β-glucan may be or be derived from β(1,6)-[poly-(1,3)-D-glucopyranosyl]-poly-β(1,3)-D-glucopyranose, also referred to herein as PGG (IMPRIME PGG, Biothera, Eagan, Minn.), a highly purified and well characterized form of soluble yeast-derived β-glucan. Moreover, β-glucan-based immunotherapies can involve the use of, for example, a modified and/or derivatized β-glucan such as those described in International Patent Application No. PCT/US12/36795. In other cases, β-glucan immunotherapy can involve administering, for example, a particulate-soluble β-glucan or a particulate-soluble β-glucan preparation, each of which is described in, for example, U.S. Pat. No. 7,981,447.

Biomarker research demonstrated differences among subjects in the ability of their neutrophils and monocytes to bind IMPRIME PGG. Binding of IMPRIME PGG to these cells correlated with the subjects' immunomodulatory response to IMPRIME PGG. Moreover, IMPRIME PGG binding to neutrophils and monocytes involves the presence of a specific level of natural anti-β-glucan antibodies.

This disclosure provides a simple ELISA method to quantitatively measure anti-β-glucan IgG and IgM antibodies in patient serum samples. The ELISA method may be used as a biomarker assay. Cutoff levels for the biomarker assay identify biomarker positive and biomarker negative subgroups of healthy volunteers and these cutoff points correlate with binding, function, and clinical outcomes.

Early studies evaluating binding of IMPRIME PGG to neutrophils from healthy volunteers revealed subjects with different binding capabilities. High neutrophil binding (e.g., IMPRIME PGG bound to >20% of neutrophils) of IMPRIME PGG is found in ~40% of healthy volunteers. Monocyte binding of IMPRIME PGG parallels the binding potential of neutrophils in healthy volunteers. In vitro, high neutrophil binders and high monocyte binders produce more IL-8 than low binders.

Higher natural anti-β-glucan antibody levels correspond with neutrophil binding of IMPRIME PGG. High-binder serum/plasma can increase IMPRIME PGG binding to neutrophils from low binders. Anti-β-glucan antibodies in the high-binder serum can increase neutrophil IMPRIME PGG binding in low-binders in non-permissive binding conditions. For example, intravenous immunoglobulin (IVIG), which contains high natural anti-β-glucan antibody titers, can increase IMPRIME PGG binding to neutrophils from a low-binder. Natural anti-β-glucan IgG and/or IgM antibodies are involved in binding to neutrophils and monocytes. Without wishing to be bound by any particular theory, natural anti-β-glucan antibodies (e.g., IgG and IgM) bind to IMPRIME PGG. The IMPRIME PGG is opsonized via the classical pathway of complement activation. Opsonized IMPRIME PGG binds to the lectin-like domain of CR3 receptors on neutrophils and monocytes. The opsonization of IMPRIME PGG (i.e., iC3b deposition) occurs as a result of the classical pathway of complement activation after antibody binding. Several functional markers are modulated during the process of neutrophil and/or monocyte binding of IMPRIME PGG such as, for example, C4a, C5a and SC5b-9.

IMPRIME PGG binding to neutrophils and/or monocytes in whole blood samples can be reproducibly measured using assays that use, for example, flow cytometry. The use of whole blood for such assays, however, presents certain challenges. For example, it requires live, healthy cells so that blood samples need to be received and processed within 24 hours of collection. Thus, shipping conditions and environmental factors can damage the blood cells. Such assays also required control blood samples from known high binder and low binder subjects. Finally, although a conceptually simple assay, flow cytometry technology is not common in many clinical labs. Thus, the flow cytometry-based assay is not a practical assay for clinical development.

This disclosure provides a method that involves simple quantitative ELISA to measure endogenous anti-β-glucan antibody levels in human serum samples. The method overcomes the challenges presented by the flow cytometry-based assay for the development of a practical clinical test. Serum-based ELISA assays are common clinical assays and can be performed by most clinical labs. Moreover, serum samples can be frozen resulting in easier storage, shipping and consistency in assay performance.

In some embodiments, the β-glucan may be derived from yeast such as, for example, Saccharomyces cerevisiae. In some embodiments, the β-glucan can include a β-1,3/1,6 glucan such as, for example, β(1,6)-[poly-(1,3)-D-glucopyranosyl]-poly-β(1,3)-D-glucopyranose.

In some embodiments, β-glucan bound to the immune cells may be detected by contacting the sample with a monoclonal antibody that specifically binds to the β-glucan.

The monoclonal antibody may be any monoclonal antibody that specifically binds to the β-glucan. As used herein, "specific" and variations thereof refer to having a differential or a non-general (i.e., non-specific) affinity, to any degree, for a particular target. Exemplary monoclonal antibodies that specifically bind β-glucan include, for example, monoclonal antibodies identified as BfD I, BfD II, BfD III, and/or BfD IV (Biothera, Eagan, Minn.), each of which is described in U.S. Pat. No. 6,294,321.

Traditional approaches to measuring the amount of antibody in serum typically involve the use of an ELISA in the context of an assay in which a sample is serially diluted. The serial dilutions are subjected to the ELISA assay and the amount of antibody in the serum sample is estimated based on the greatest dilution of serum sample that generates a positive assay response. The resulting titer value is an estimate within dilutional ranges and not an exact measurement of the amount of antibodies. Serial dilution methods are frequently used in serology to determine the amount of antibody (titer level) in the serum. Determining titer levels is frequently used to evaluate antibody responses to vaccines. In serial dilution methods, however, one cannot measure directly the exact amount of antibody that is produced. Instead, one can only estimate the amount of antibody produced within a dilutional range. Titer levels are, therefore, not amenable to standard statistical analyses in a straightforward manner without modifications of the data and/or the statistical analytical techniques.

In contrast, this disclosure provides an ELISA-based method that measures natural anti-β-glucan antibodies to IMPRIME PGG in human serum. The method involves quantitatively measuring the amount of natural anti-β-glucan antibodies as either Relative Antibody Units (RAU) or anti-β-glucan antibody concentration within statistical requirements. This is accomplished by generating a titer and correlating either RAU data or antibody concentration data (both determined from a calibration curve) in the same assay. Thus, the methods described herein involve generating internal standard curves from serum with an established level of natural anti-β-glucan antibody. Moreover, the methods provide a better method of quantitatively measuring relative or actual anti-β-glucan antibodies than measuring titers.

The methods can be used to measure anti-β-glucan IgG and/or anti-β-glucan IgM. The computation of RAU for IgG and/or IgM is shown in Table 7. The computation of antibody concentration for IgG and/or IgM is shown in Table 8 and Table 9, respectively. The methods provide intra-assay precision—i.e., reproducibility between plates. The methods also provide inter-assay precision—i.e., reproducibility between assays and/or assay days for control and test serum samples. The methods allow one to evaluate multiple samples analyzed on different test plates by a single operator. Thus, the methods provide reliable, reproducible results whether in the hands of a single operator analyzing multiple samples in a single day or in the hands of multiple operators over the course of multiple days.

Figure 2:
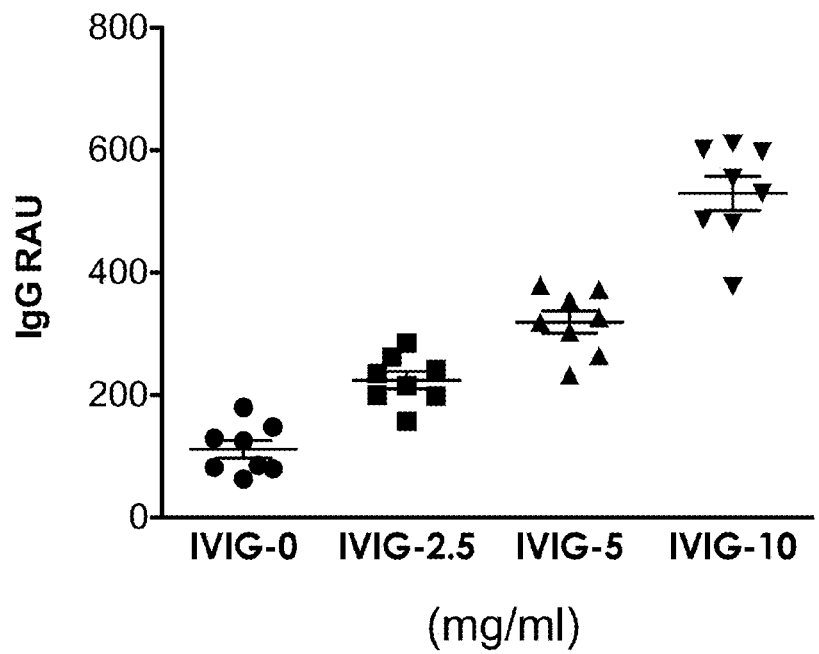
FIG. 2. Whole blood from eight healthy volunteers with low levels of IgG (RAU<200) and IgM (RAU<100) anti-beta glucan antibodies were spiked with increasing concentrations of IVIG (0, 2.5, 5 and 10 mg/ml). Plasma was removed and RAU values determined for each sample.
Figure 3:
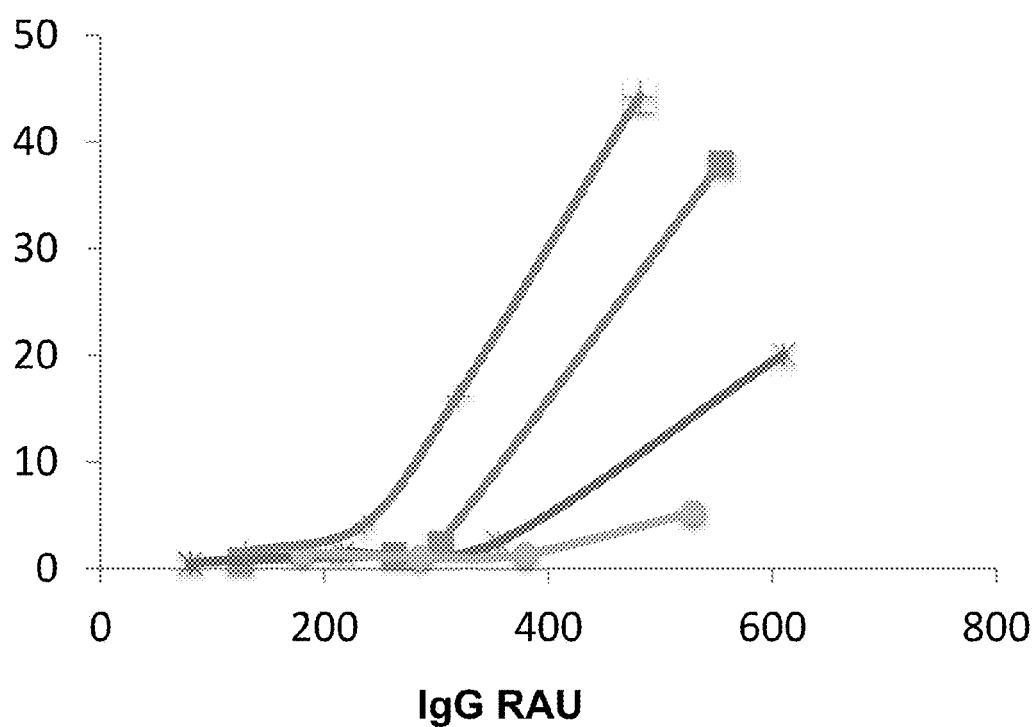
FIG. 3. A sample of blood from four healthy volunteers with low levels of IgG (RAU<200) and IgM (RAU<100) anti-beta glucan antibodies was spiked with increasing concentrations of IVIG (0, 2.5, 5 and 10 mg/ml). Whole blood cells were treated with IMPRIME PGG at 10 μg/mL and incubated at 37° C. for 30 min and analyzed for neutrophil binding.
Figure 4:
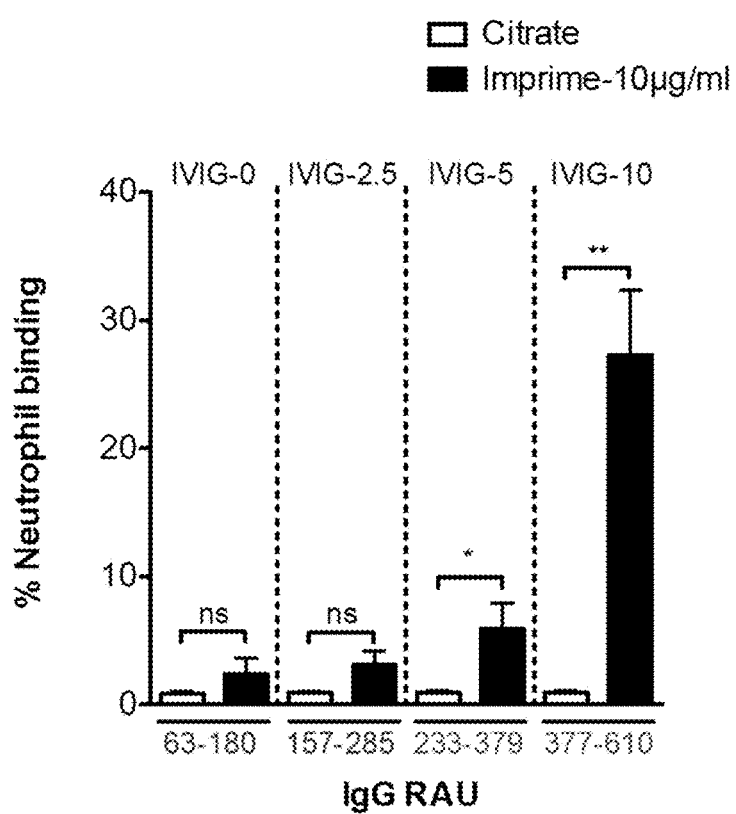
FIG. 4. Whole blood cells from eight healthy volunteers with low levels of IgG (RAU<200) and IgM (RAU<100) anti-beta glucan antibodies were cultured with IMPRIME PGG (10 mg/ml) and IVIG (0, 2.5, 5 and 10 mg/ml) and evaluated for IMPRIME PGG binding and function (30 min incubation for complement analysis; 2 hrs for binding and receptor modulation; overnight culture for cytokines).
Figure 4:
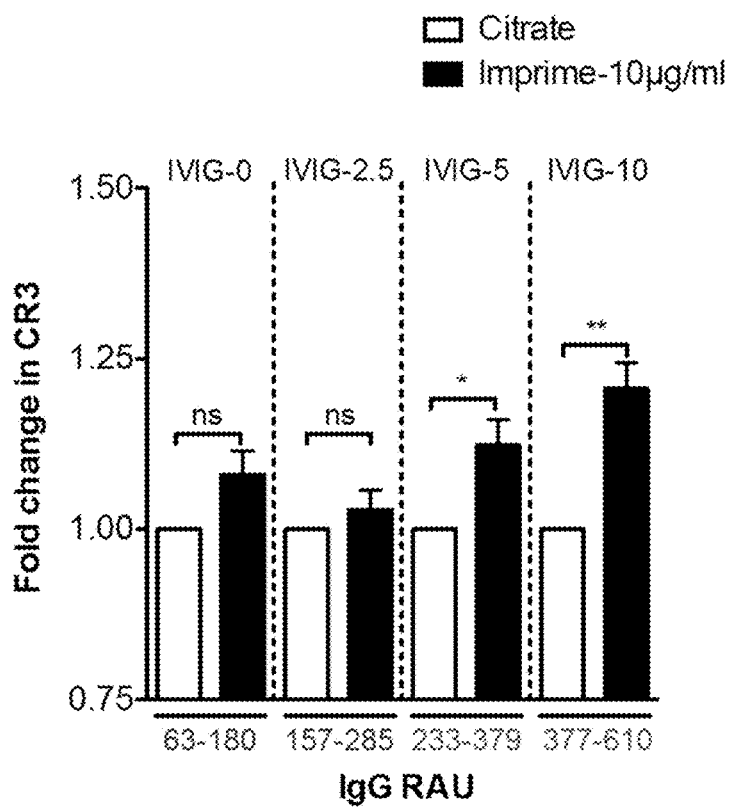
Figure 5:
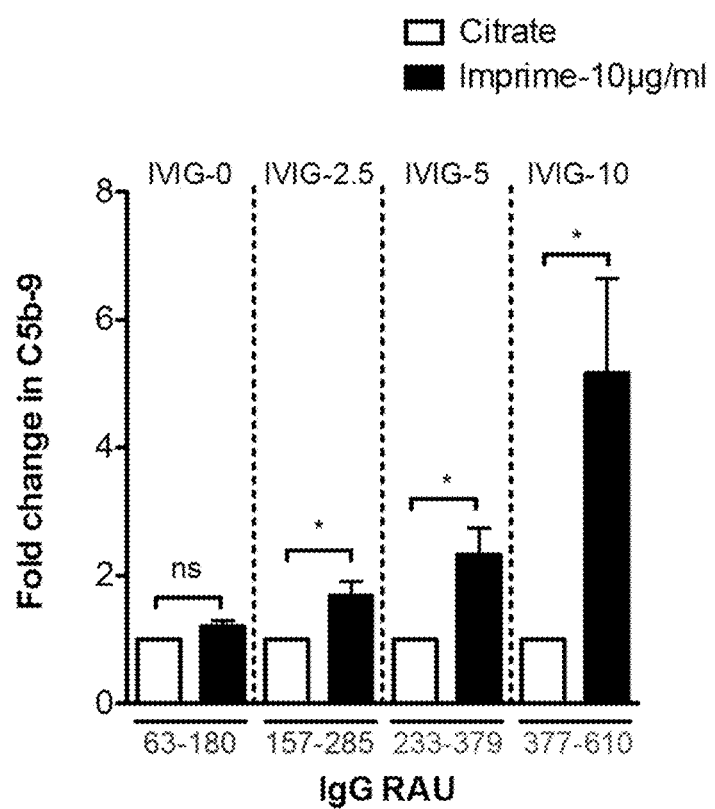
FIG. 5. Whole blood cells from eight healthy volunteers with low levels of IgG (RAU<200) and IgM (RAU<100) anti-beta glucan antibodies were cultured with IMPRIME PGG (10 mg/ml) and IVIG (0, 2.5, 5 and 10 mg/ml) and evaluated for IMPRIME PGG induced SC5b-9 release.
Figure 6:
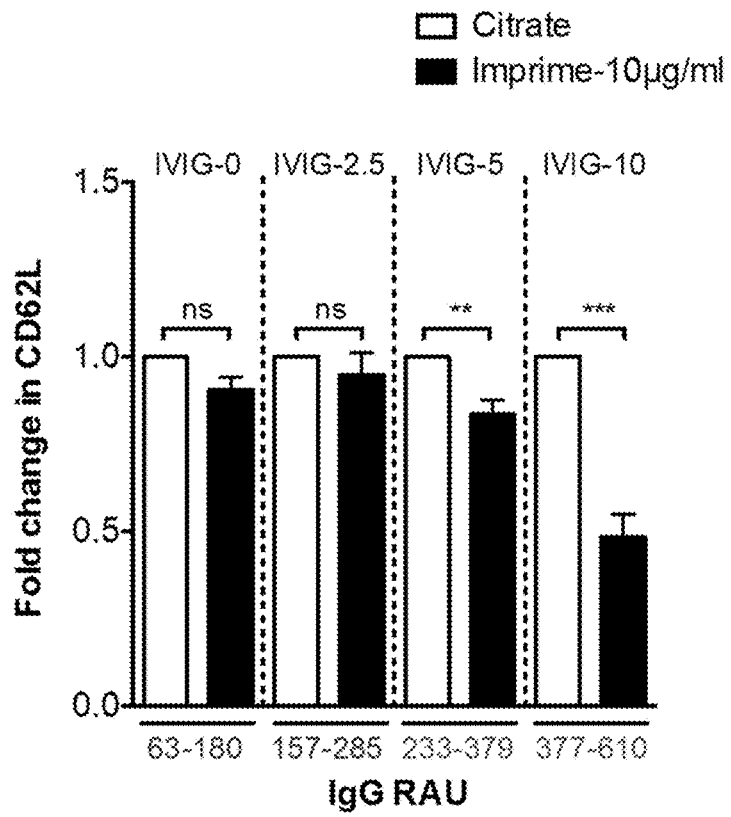
FIG. 6. Whole blood cells from eight healthy volunteers with low levels of IgG (RAU<200) and IgM (RAU<100) anti-beta glucan antibodies were incubated with IMPRIME PGG (10 mg/ml) and IVIG (0, 2.5, 5, and 10 mg/ml) and evaluated for IMPRIME PGG induced CD62L shedding (flow-cytometry) on neutrophils and IL-8 production (ELISA).
Figure 6:
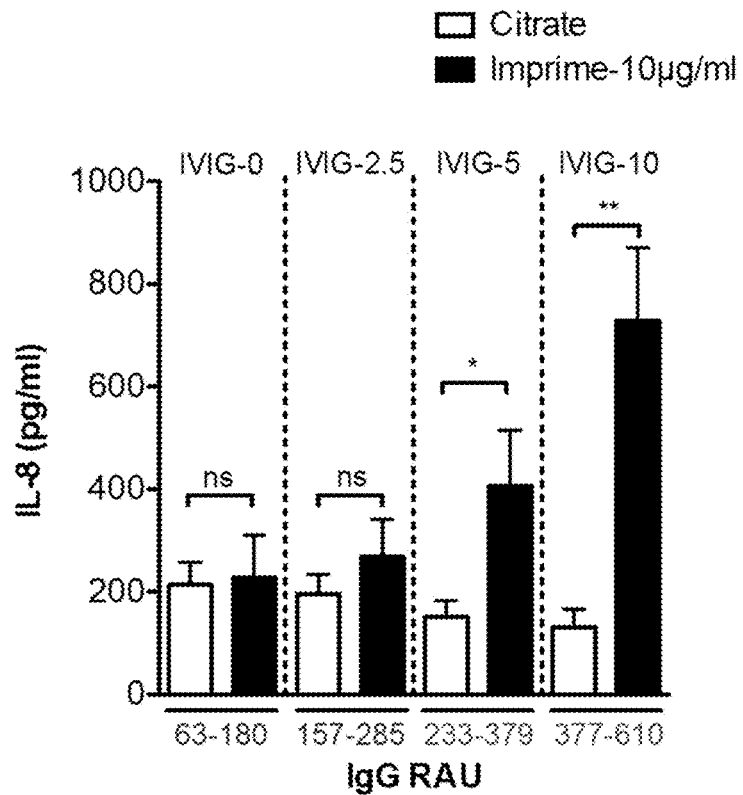
Figure 7:
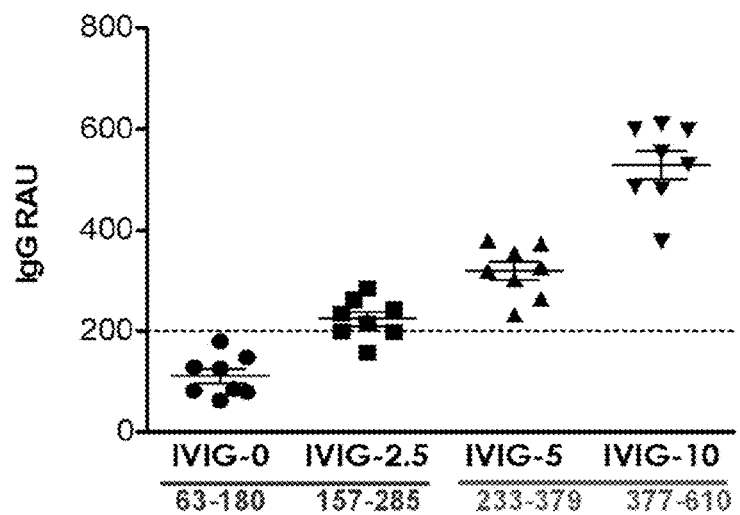
FIG. 7. The RAU required for binding and function varies by individual. Hence, the objective of the biomarker cutoff is to identify an RAU level that will exclude individuals who will not respond to IMPRIME PGG and enrich for biomarker positive subjects that have a higher probability to respond. Binding and functional data indicate the most activity to occur in the ≥IVIG-5 group (RAU 233-610) and therefore, further analysis for the IgG cutoff should be focused on the RAU range above 200.

The anti-β-glucan antibody level required for binding and function can vary by individual. FIG. 2 shows a dose-dependent increase in anti-β-Glucan IgG RAU levels with IVIG. The method involves using a biomarker cutoff to identify an RAU level that will exclude individuals who will not respond to IMPRIME PGG and enrich for biomarker positive subjects that have a higher probability to respond. Binding and functional data indicate the most activity to occur in the ≥IVIG-5 group (RAU 233-610) and therefore, further analysis for the IgG cutoff should be focused on the RAU range above 200. (FIG. 7).

An initial study in 32 healthy volunteers was performed to establish the specific minimum level of natural anti-β-glucan antibodies (RAUs of IgG and/or IgM) necessary for binding and function of IMPRIME PGG in neutrophils or monocytes. The minimum levels quantified as anti-β-glucan antibody concentrations of IgG and/or IgM were further optimized using a larger cohort of healthy subjects (n=143) and confirmed the significance of elevated anti-β-glucan antibody levels with respect to binding of IMPRIME PGG to neutrophils and monocytes, IMPRIME PGG-induced functional changes and clinical outcomes. Subjects with anti-β-glucan antibody levels conducive to IMPRIME PGG binding to neutrophils and monocytes are considered "biomarker positive." The bioassay can allow one to identify subjects in a clinical setting with anti-β-glucan antibody levels that are too low for IMPRIME PGG binding to neutrophils and monocytes ("biomarker negative") so that they can either receive alternative treatment or receive anti-β-glucan antibody treatments so that they better respond to therapy that involves IMPRIME PGG. Alternatively, a biomarker positive individual may be more immune competent than a biomarker negative individual and, thus, may respond better to immunotherapy drugs.

When using the RAU method, an individual can be biomarker positive by possessing an IgG RAU of at least a minimum IgG RAU predetermined value and/or possessing an IgM RAU of at least a minimum IgM RAU predetermined value. In some embodiments, the IgG RAU predetermined value can be at least 200 such as, for example, at least 205, at least 210, at least 215, at least 220, at least 225, at least 230, at least 235, at least 240, at least 245, at least 250, at least 255, at least 260, at least 265, at least 270, or at least 275. In some embodiments, the IgM RAU predetermined value can be at least 300 such as, for example, at least 305, at least 310, at least 315, at least 320, at least 325, at least 330, at least 335, at least 340, at least 345, at least 350, at least 355, at least 360, at least 365, at least 370, or at least 375. That is, an IgG RAU of, for example, at least 200 or an IgM RAU of, for example, at least 300 reasonably correlates with an individual that exhibits at least 5% of neutrophils binding β-glucan and the neutrophil and monocyte functional modulation associated with β-glucan "high binder" status.

Figure 8:
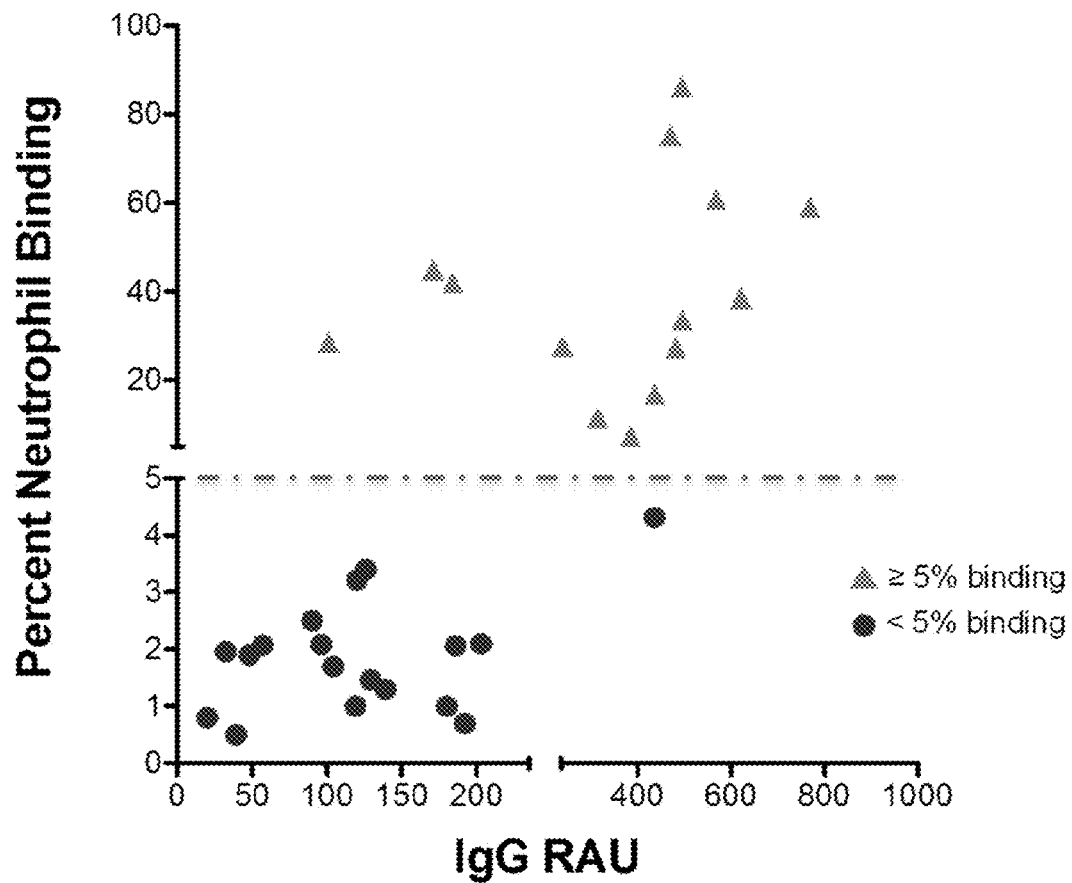
FIG. 8. Healthy volunteer neutrophil binding of IMPRIME PGG plotted by IgG RAU level.
Figure 9:
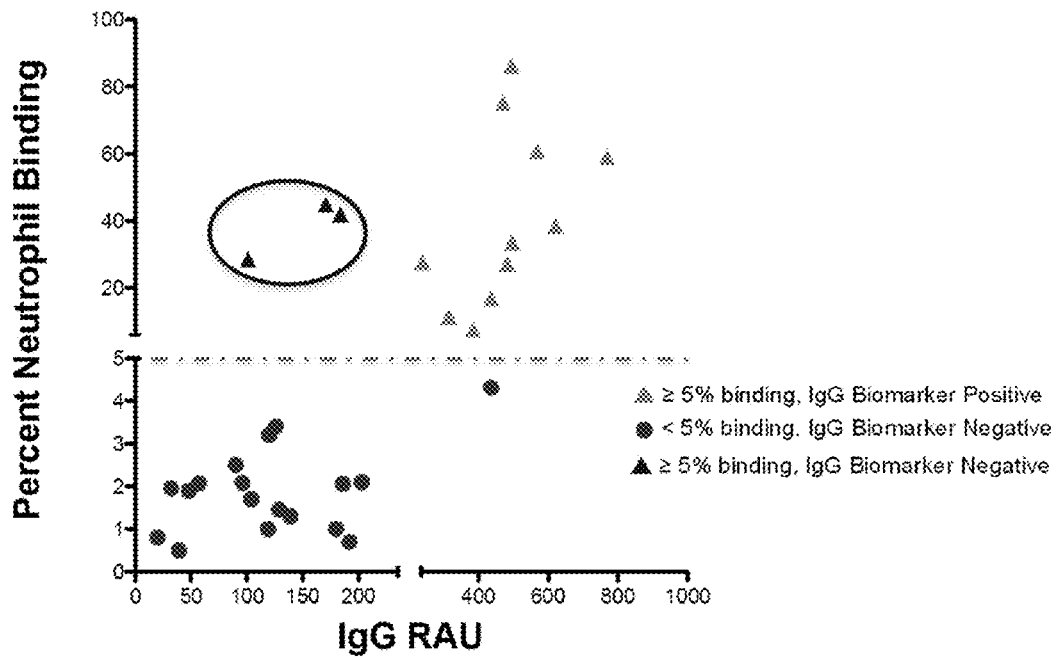
FIG. 9. Healthy volunteer neutrophil binding of IMPRIME PGG plotted by IgG RAU level. The circled volunteers were high neutrophil binders with low IgG RAU but had high IgM RAU, thus, can be removed from IgG RAU analysis.
Figure 10:
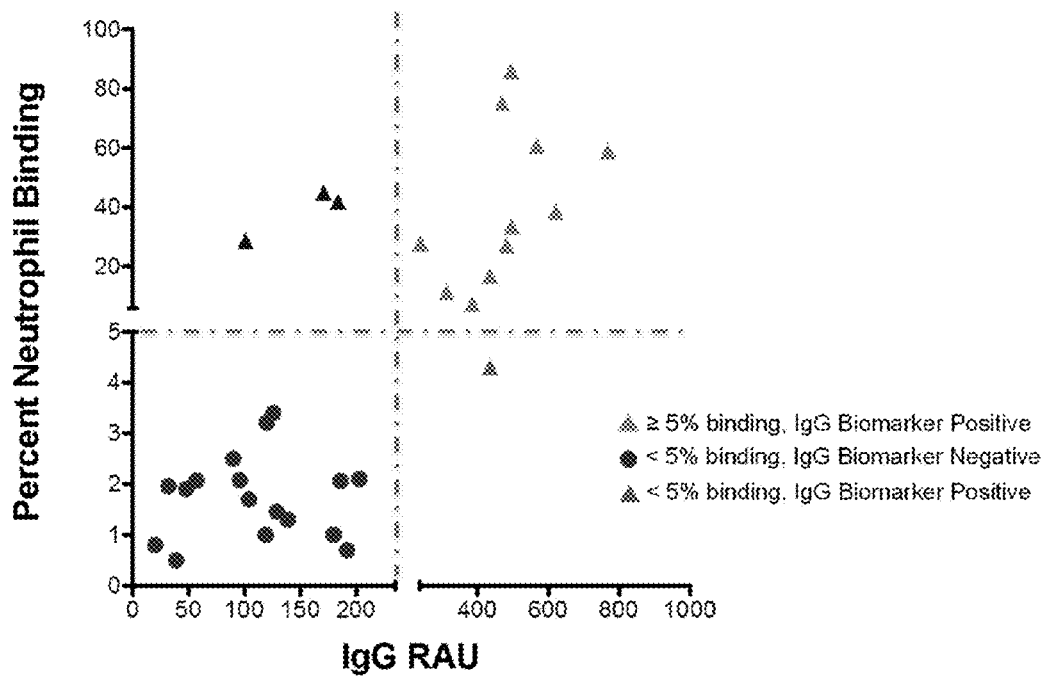
FIG. 10. Healthy volunteer neutrophil binding of IMPRIME PGG plotted by IgG RAU level. An IgG RAU cutoff of 235 dissociated volunteers whose RAU was sufficient to facilitate binding (biomarker positive) versus volunteers whose RAU was not sufficient to facilitate binding (biomarker negative).
Figure 11:
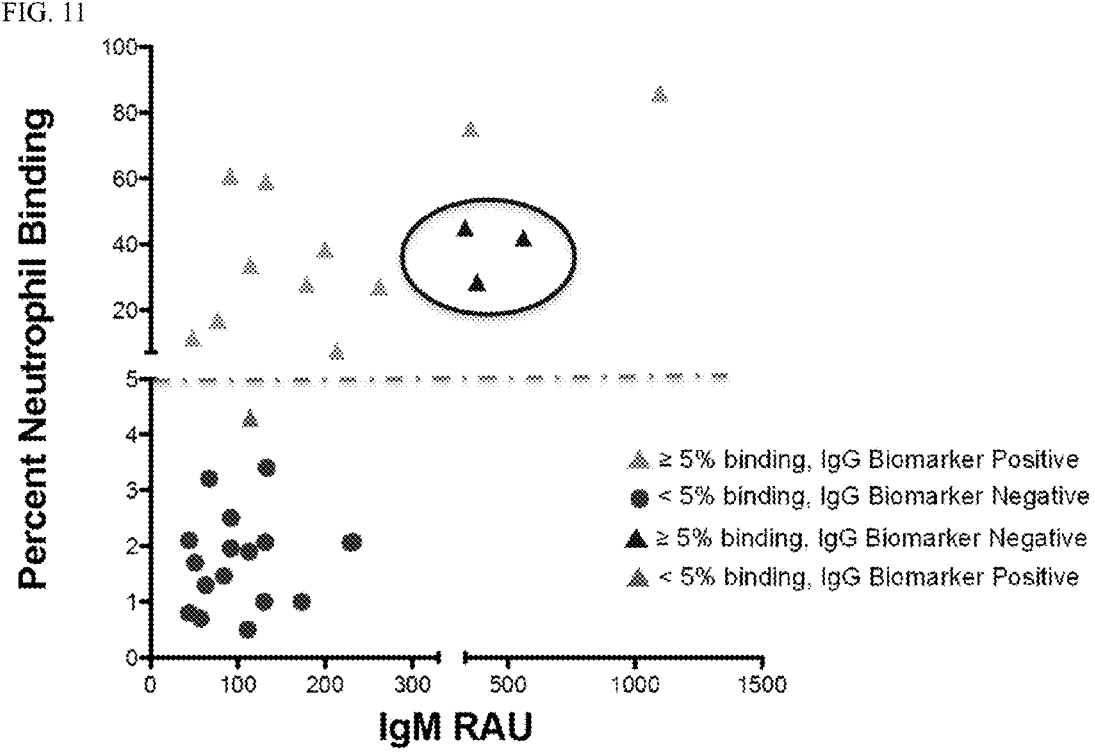
FIG. 11. Healthy volunteer neutrophil binding of IMPRIME PGG plotted by IgG RAU level. The circled individuals are IgG biomarker negative but high IgM RAU.
Figure 12:
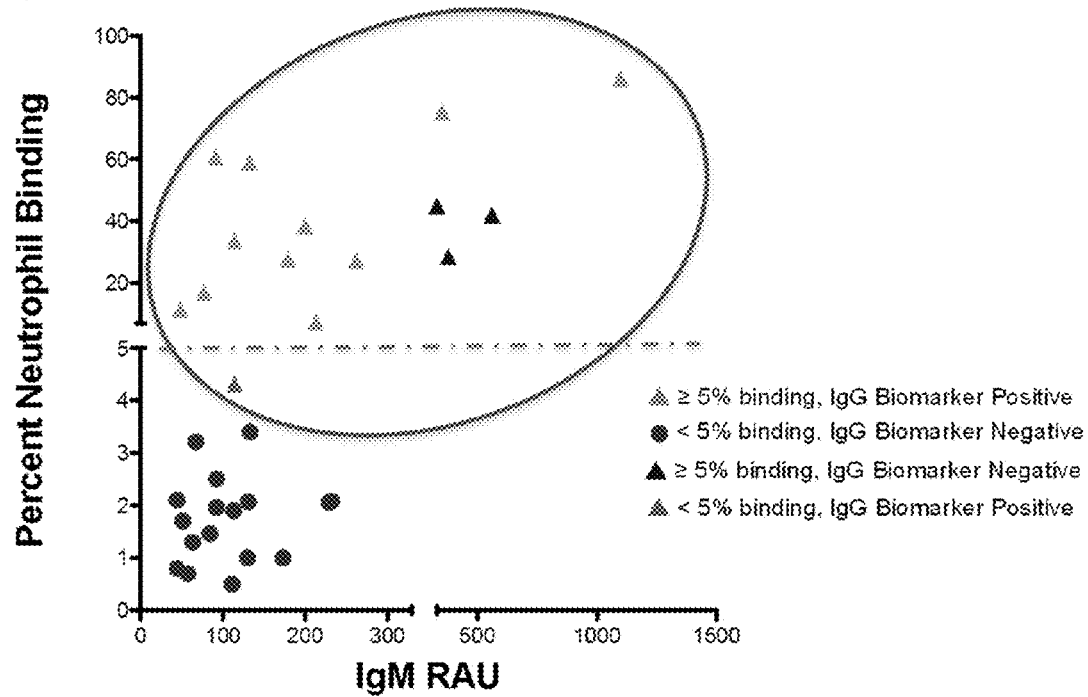
FIG. 12. Healthy volunteer neutrophil binding of IMPRIME PGG plotted by IgG RAU level. The non-blue volunteers circled in green were already biomarker positive based on high IgG RAU, thus, can be removed from IgM RAU analysis.
Figure 13:
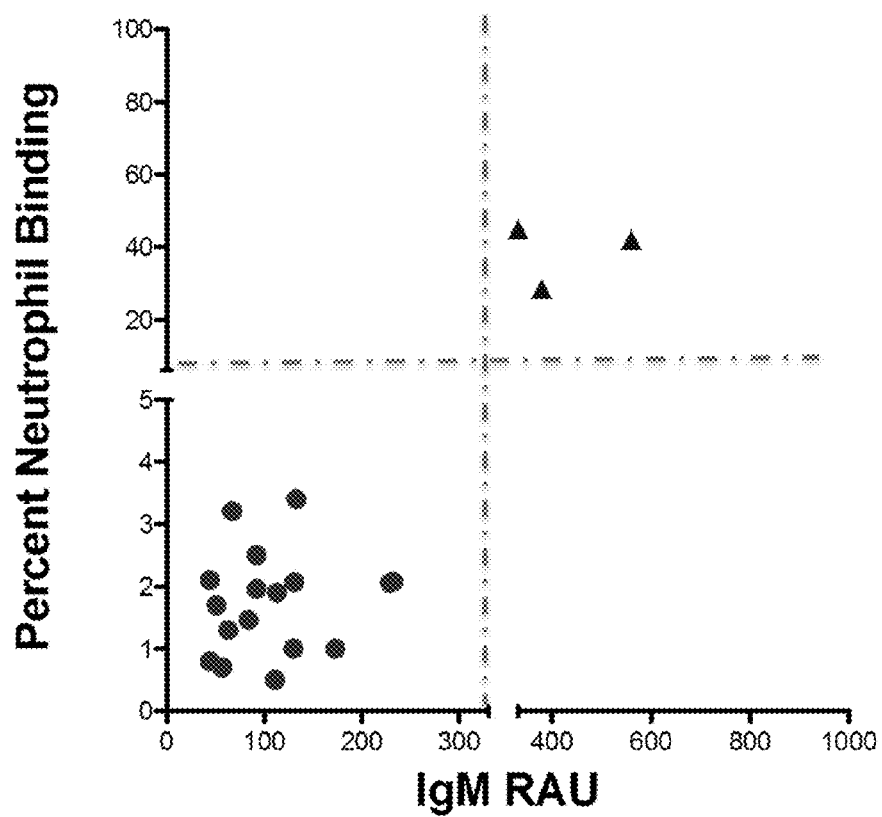
FIG. 13. Healthy volunteer neutrophil binding of IMPRIME PGG plotted by IgG RAU level. An IgM RAU cutoff of 330 dissociated volunteers whose RAU was sufficient to facilitate binding (biomarker positive) versus volunteers whose RAU was not sufficient to facilitate binding (biomarker negative).

For example, FIG. 8 shows a plot of the percent neutrophil binding for each of the 32 healthy volunteers as a function of the computed IgG RAU. The horizontal line at 5% neutrophil binding delineates "high binders" from "low binders." To distinguish between those volunteers whose IgG RAU was too low to bind more than 5% neutrophils and those whose IgG RAU was sufficient to exhibit at least 5% of their neutrophils binding β-glucan, we established a cut off line at an IgG RAU of 235 (FIG. 10), the closest value under the lowest IgG RAU value showing higher than 5% of neutrophils binding β-glucan (239). We subsequently evaluated the level of the three individuals who had greater than 5% of neutrophils binding β-glucan, but were IgG biomarker negative (FIG. 9, circled). These three individuals were IgG biomarker negative—i.e., IgG RAU of less than 235—but nevertheless exhibited at least 5% of their neutrophils binding β-glucan. When neutrophil binding was plotted as a function of IgM RAU, an IgM RAU cutoff value of 330 was established. (FIG. 13).

When using the antibody concentration method, which is further optimized, an individual can be biomarker positive by possessing an IgG anti-β-glucan antibody concentration of at least a minimum IgG anti-β-glucan antibody concentration predetermined value and/or possessing an IgM anti-β-glucan antibody concentration of at least a minimum IgM anti-β-glucan antibody concentration predetermined value. IMPRIME PGG binding and anti-β-glucan antibody concentration measurements from serum derived from the same draw of whole blood were evaluated in healthy volunteers, N=143. The range of IgG and IgM anti-β-glucan antibody concentrations determined for the N=143 individuals was 1.13-209.8 µg/ml (7.8-1447.8 RAU/ml) and 5.3-2032.7 µg/ml (12.8-4878.4 RAU/ml), respectively. Both neutrophils and monocytes demonstrated greater than 5% binding more frequently at approximately 14 µg/ml (100 RAU/ml) and 42 µg/ml (100 RAU/ml) IgG and IgM anti-β-glucan antibody levels, respectively.

Therefore, in some embodiments, the IgG anti-β-glucan antibody concentration predetermined value can be at least 14 µg/ml (100 RAU) such as, for example, at least 15, at least 20, at least 25, at least 30, at least 35, at least 40, at least 45, at least 50, at least 55, at least 60, at least 65, at least 70, at least 75 or at least 80 µg/ml (100 RAU). In some embodiments, the IgM anti-β-glucan antibody concentration predetermined value can be at least 42 µg/ml such as, for example, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320, at least 330, at least 340, at least 350, at least 360, at least 370, at least 380, at least 390, at least 400, at least 410, at least 420, at least 430, at least 440, at least 450, at least 460, at least 470, at least 480, at least 490, at least 500, at least 510, at least 520, at least 530, at least 540 or at least 550 µg/ml (100 RAU). That is, an IgG anti-β-glucan antibody concentration of, for example, at least 14 µg/ml or an IgM anti-β-glucan antibody concentration of, for example, at least 42 µg/ml reasonably correlates with an individual that exhibits at least 5% of neutrophils or monocytes binding β-glucan and the neutrophil and monocyte functional modulation associated with β-glucan "high binder" status.

Figure 23:
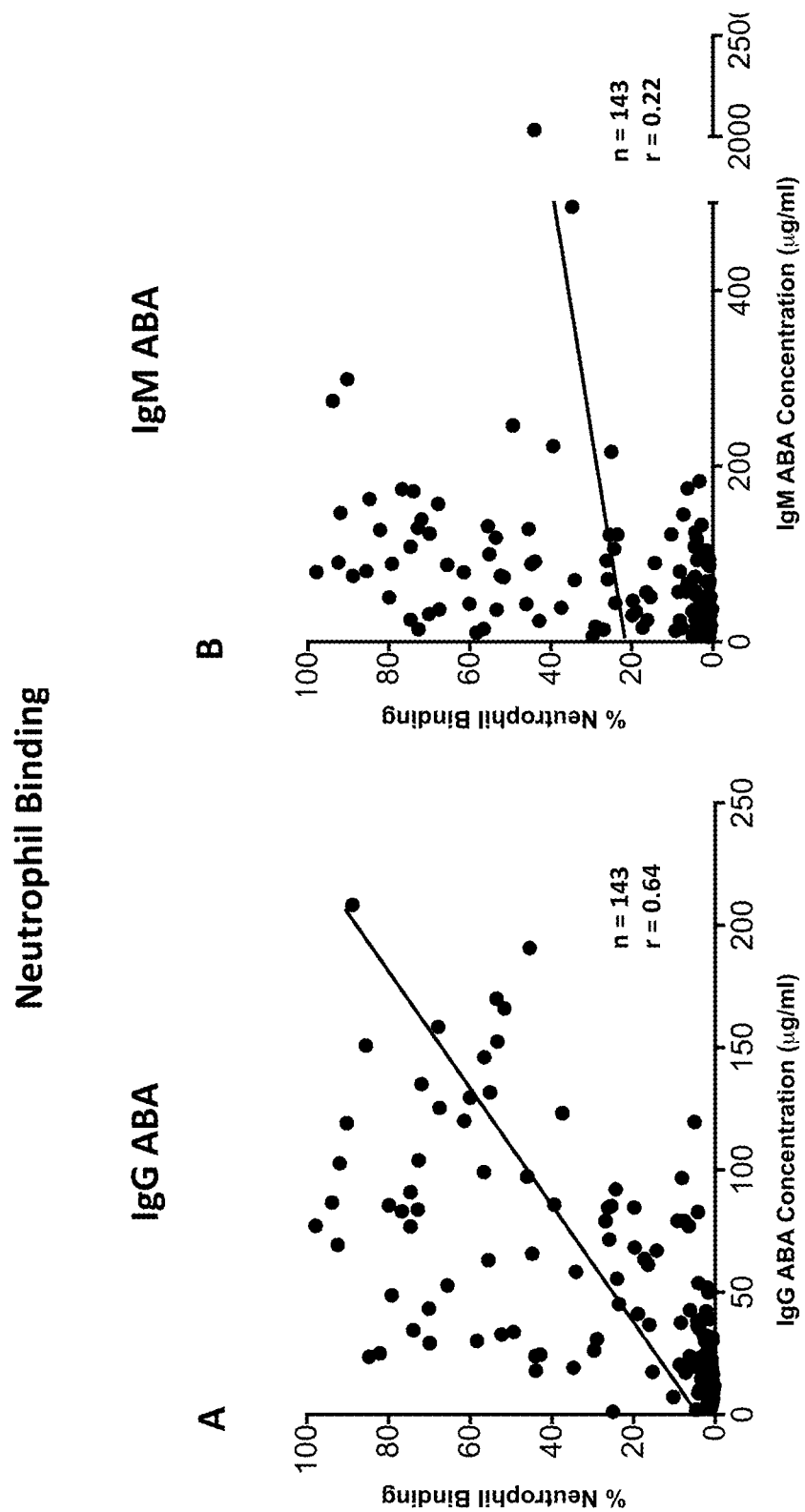
FIG. 23. (A) Correlation of IgG anti-β-glucan antibody concentrations with neutrophil binding of IMPRIME PGG in whole blood of healthy subjects; (B) Correlation of IgM anti-β-glucan antibody concentrations with neutrophil binding of IMPRIME PGG in whole blood of healthy subjects.
Figure 24:
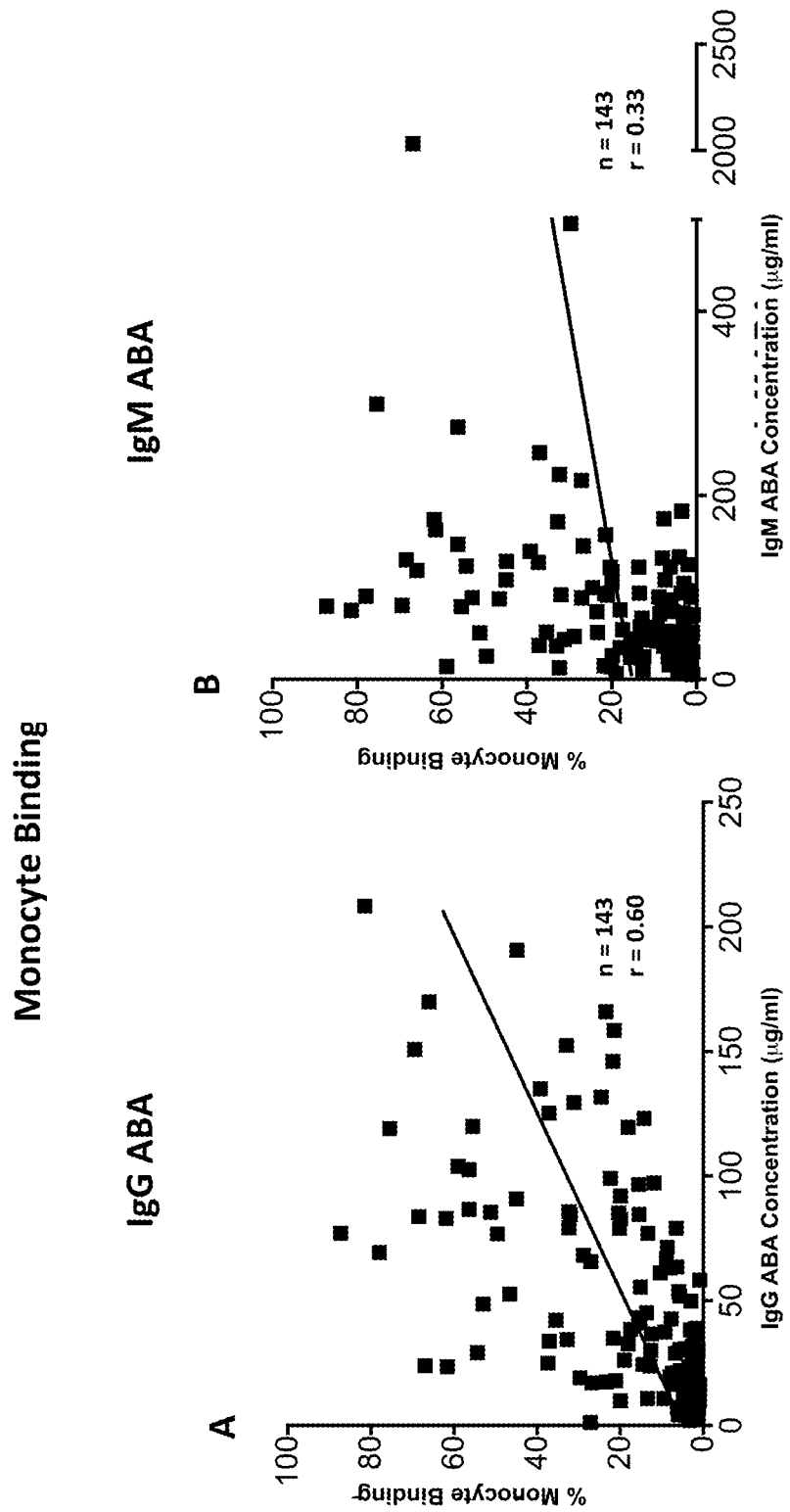
FIG. 24. (A) Correlation of IgG anti-β-glucan antibody concentrations with monocyte binding of IMPRIME PGG in whole blood of healthy subjects; (B) Correlation of IgM anti-β-glucan antibody concentrations with monocyte binding of IMPRIME PGG in whole blood of healthy subjects.

FIG. 23 and FIG. 24 show plots of the percent neutrophil and monocyte binding for each healthy volunteer as a function of the computed (A) IgG and (B) IgM anti-β-glucan antibody concentrations. As shown, IMPRIME PGG binding to neutrophils and monocytes increases as IgG and/or IgM anti-β-glucan antibody concentrations increase.

Figure 25:
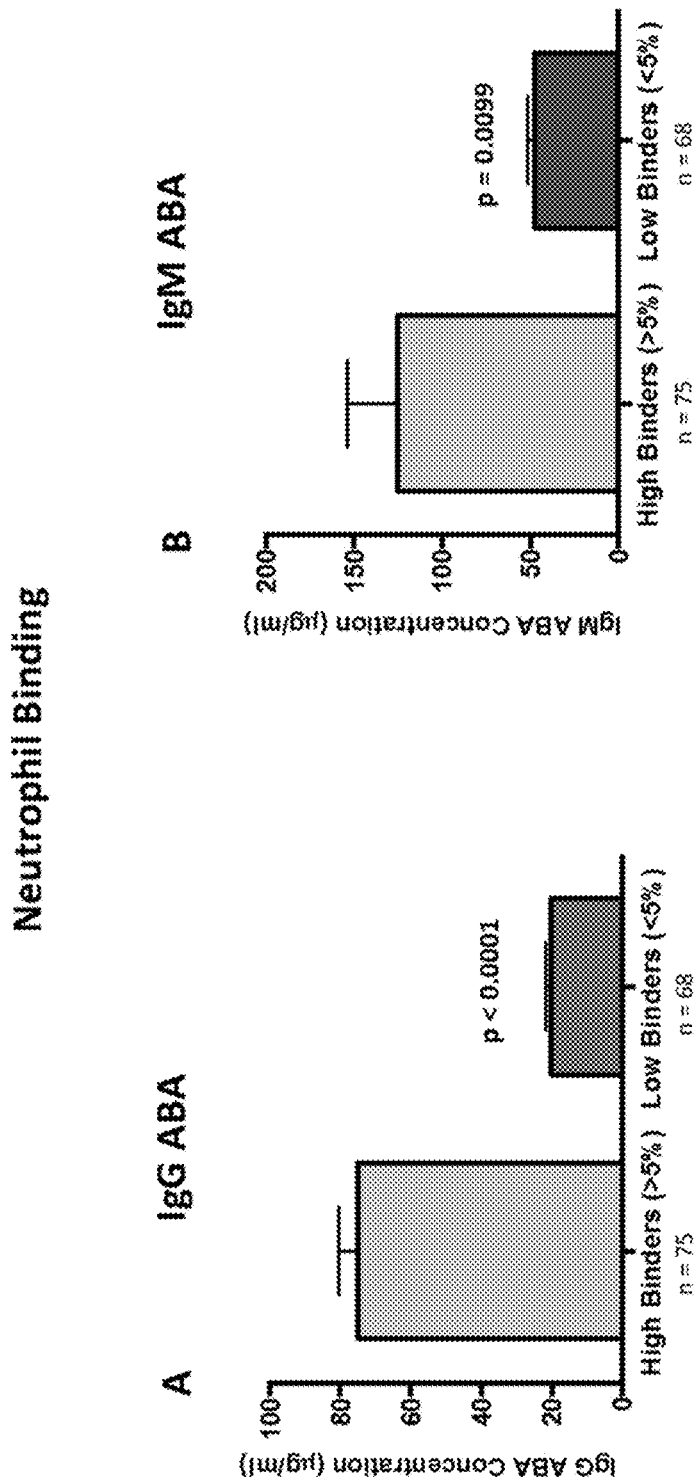
FIG. 25. (A) Correlation of IgG anti-β-glucan antibody concentrations with neutrophil binding of IMPRIME PGG based on high vs. low binder status; (B) Correlation of IgM anti-β-glucan antibody concentrations with neutrophil binding of IMPRIME PGG based on high vs. low binder status.
Figure 26:
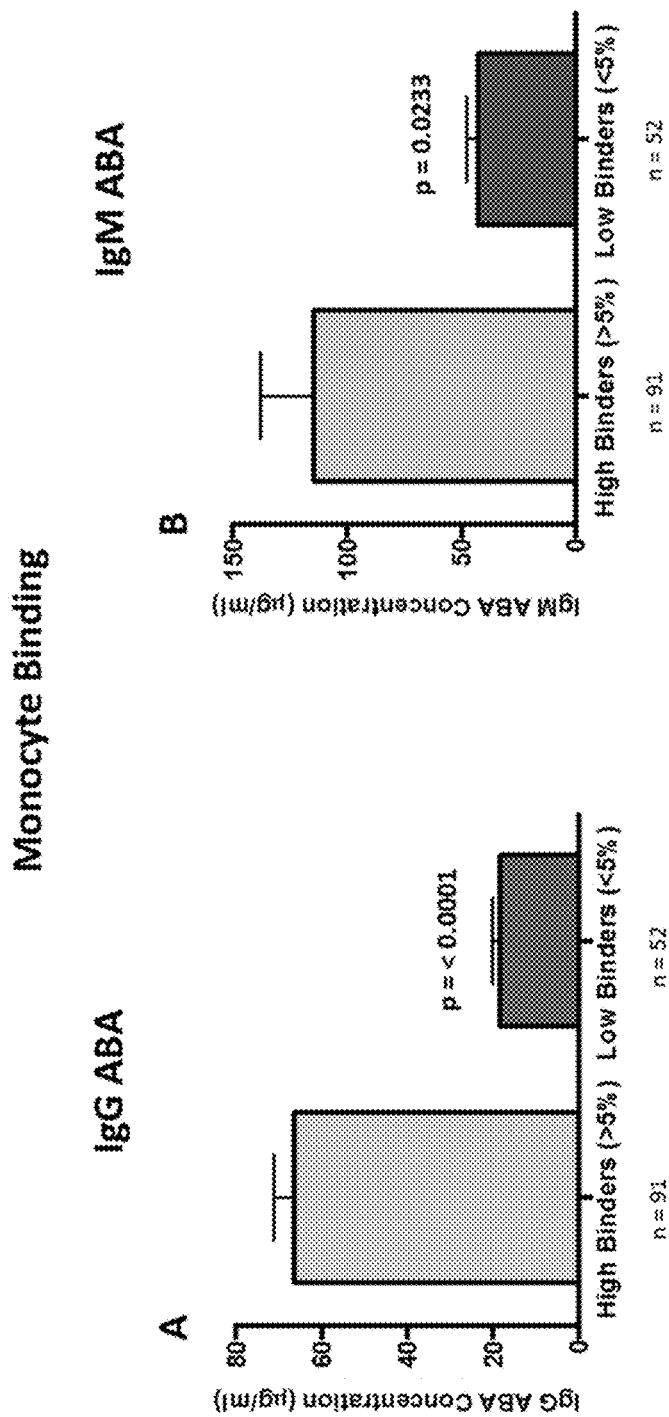
FIG. 26. (A) Correlation of IgG anti-β-glucan antibody concentrations with monocyte binding of IMPRIME PGG based on high vs. low binder status; (B) Correlation of IgM anti-β-glucan antibody concentrations with monocyte binding of IMPRIME PGG based on high vs. low binder status.

As shown in FIG. 25 and FIG. 26, there was strong correlation between IgG and IgM anti-β-glucan antibody concentrations and both neutrophil and monocyte binding at a 5% binding level, distinguishing high and low IMPRIME PGG binders. There was no correlation between anti-β-glucan antibody concentrations and age, gender, or total immunoglobulin (data not shown).

Figure 27:
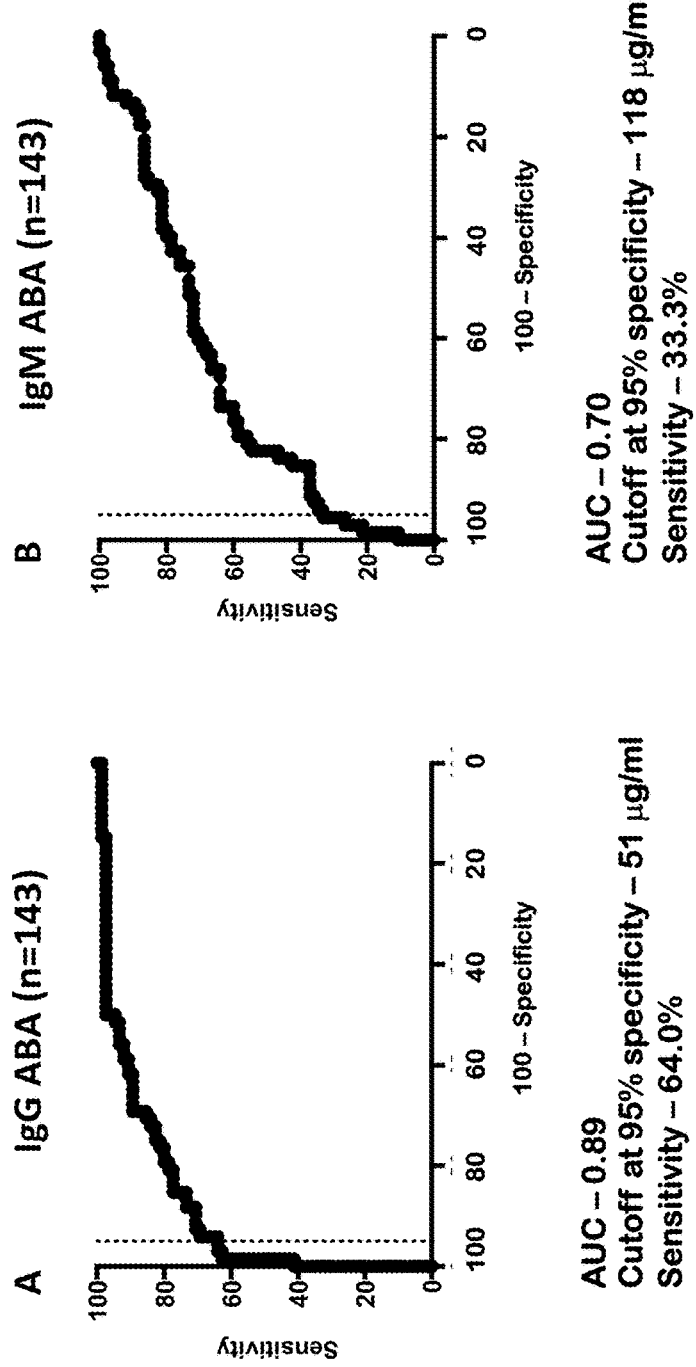
FIG. 27. (A) IgG ROC curve analysis based on neutrophil binding; (B) IgM ROC curve analysis based on neutrophil binding.
Figure 28:
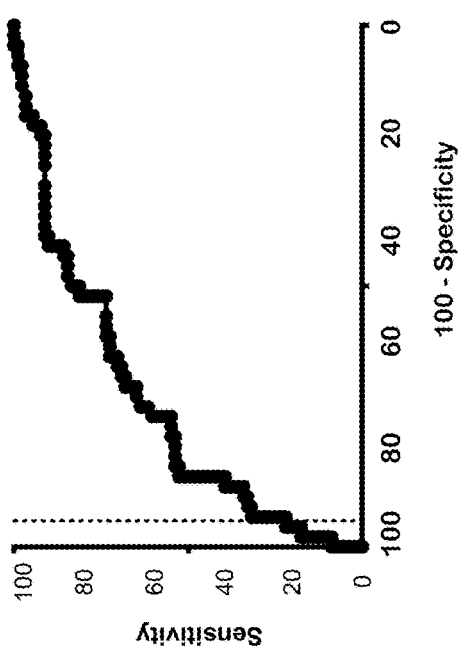
FIG. 28. (A) IgG ROC curve analysis based on monocyte binding; (B) IgM ROC curve analysis based on monocyte binding.
Figure 28:
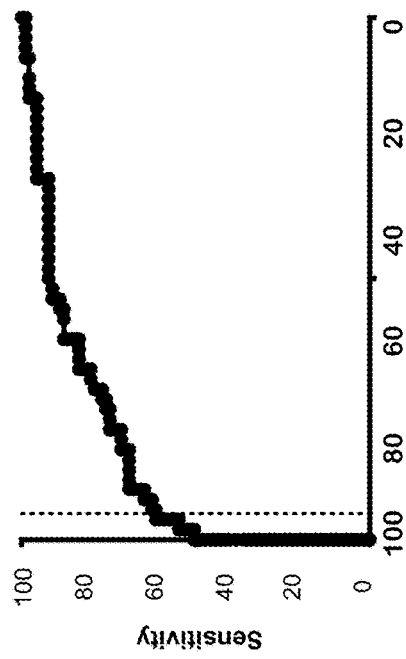

Next, exploratory cutoffs of anti-β-glucan antibody concentrations were investigated in the 143 healthy volunteers. Using a 5% level for both neutrophil and monocyte binding of IMPRIME PGG, the correlation between the sensitivity and specificity of anti-β-glucan concentrations was determined using ROC curve analysis (FIG. 27 and FIG. 28). At an initial exploratory specificity of 95% for binding, anti-β-glucan antibody concentration cutoffs were determined and used to calculate both the prevalence of the biomarker in the healthy population and its sensitivity for determining binding status. The results are shown in Table 1.

TABLE 1

| Parameter | Based on Neutrophil Binding | | Based on Monocyte Binding | |
|---|---|---|---|---|
| | IgG | IgM | IgG | IgM |
| Cutoff (µg/ml) | 51 | 118 | 40 | 126 |
| Prevalence | 36% | 20% | 41% | 15% |
| (Biomarker Positive) | 46% Overall | | 48% Overall | |
| Sensitivity | 64% | 33% | 62% | 22% |
| (Biomarker Positive) | 75% Overall | | 66% Overall | |

Positive IgG anti-β-glucan biomarker status is highly correlated with in vitro IMPRIME PGG biological activity using either set of cutoffs. However, as indicated by ROC curve analysis, similar sensitivities at different cutoffs indicate a range of anti-β-glucan antibody concentrations that correlate with the biological activity of IMPRIME PGG.

Therefore, various anti-β-glucan antibody concentration cutoffs were investigated and functional endpoints were used to determine whether the cutoffs reasonably segregate individuals into high binder and low binder (biomarker positive and biomarker negative) status. IL-8 production was used as the functional endpoint to explore the range of IgG anti-β-glucan antibody concentration cutoffs. Results are shown in Table 2.

TABLE 2

| Cutoffs (RAU/µg per ml) | Binding to Neutrophils | Binding to Monocytes | IL-8 Production | Approximate Specificity/ Sensitivity |
|---|---|---|---|---|
| 100/14 | <0.0001 | <0.0001 | 0.0132 | 44.90/92.55 |
| 125/18 | <0.0001 | <0.0001 | 0.0019 | 59.18/88.30 |
| 150/22 | <0.0001 | <0.0001 | 0.0002 | 69.39/79.79 |
| 175/25 | <0.0001 | <0.0001 | <0.0001 | 77.55/74.47 |
| 200/29 | <0.0001 | <0.0001 | <0.0001 | 81.63/72.34 |
| 276/40 | <0.0001 | <0.0001 | <0.0001 | 97.96/60.64 |
| 351/51 | <0.0001 | <0.0001 | <0.0001 | 100/54.26 |
| 400/60 | <0.0001 | <0.0001 | <0.0001 | 100/48.94 |
| 425/62 | <0.0001 | <0.0001 | <0.0001 | 100/47.87 |
| 450/65 | <0.0001 | <0.0001 | <0.0001 | 100/45.74 |
| 475/69 | <0.0001 | <0.0001 | <0.0001 | 100/42.55 |
| 500/72 | <0.0001 | <0.0001 | <0.0001 | 100/40.43 |
| 525/76 | <0.0001 | <0.0001 | <0.0001 | 100/39.36 |
| 550/80 | <0.0001 | <0.0001 | 0.0009 | 100/35.11 |

Likewise, C4a/SC5b9 production was used as the functional endpoint to explore the range of IgM anti-β-glucan antibody concentration cutoffs. Results are shown in Table 3.

TABLE 3

| Cutoffs (RAU/µg per ml) | Binding to Neutrophils | Binding to Monocytes | C4a Production | Approximate Specificity/ Sensitivity |
|---|---|---|---|---|
| 100/42 | 0.0001 | <0.0001 | N/A | 67.35/68.09 |
| 150/63 | <0.0001 | <0.0001 | N/A | 77.55/54.26 |
| 200/83 | <0.0001 | <0.0001 | 0.1331 | 85.71/42.55 |
| 250/104 | <0.0001 | <0.0001 | 0.0587 | 93.88/30.85 |
| 300/125 | <0.0001 | <0.0001 | 0.0363 | 95.92/21.28 |
| 350/146 | <0.0001 | <0.0001 | 0.0869 | 97.96/14.89 |
| 400/167 | 0.0022 | 0.0007 | N/A | 97.96/11.7 |
| 450/188 | 0.0034 | 0.0004 | N/A | 100/8.51 |
| 500/208 | 0.0034 | 0.0004 | N/A | 100/7.44 |
| 550/229 | 0.0016 | 0.0003 | N/A | 100/6.38 |

As is evident from the data, specific IgG anti-β-glucan antibody concentration or RAU cutoff can be selected depending on the combination of specificity and sensitivity deemed to be necessary for stratifying or selection of patients in a clinical trial using ROC curve analyses. For example, a cutoff of 276 RAU/ml or 40 µg/ml would have a specificity of approximately 98% and sensitivity of 61% based on a ROC curve analysis of neutrophil and monocyte binding of IMPRIME PGG in healthy volunteers.

A reasonable range of IgM anti-β-glucan antibody concentrations or RAU cutoffs based on functional analyses, such as C4a production used here, may be 200-350 RAU/ml or 83-146 µg/ml. As above, a specific IgM anti-β-glucan antibody concentration or RAU cutoff can be selected depending on the combination of specificity and sensitivity deemed to be necessary for stratifying or selection of patients in a particular clinical trial. For example, a cutoff of 250 RAU/ml or 104 µg/ml would have a specificity of approximately 94% and sensitivity of 31% based on a ROC curve analysis of neutrophil and monocyte binding of IMPRIME PGG in healthy volunteers.

As additional support, using the cutoffs shown in Table 1, biomarker status correlates with functional changes induced by IMPRIME PGG, including activation of complement components C3a, C5a, SC5b9, modulation of neutrophil CR1, CR3, CD88, and CD62L surface marker expression, and IL-8 induction. The results are shown in Table 4.

TABLE 4

| Function | Comparison by Overall Biomarker Status[1] | |
| --- | --- | --- |
| | Neutrophil-Derived Cutoff[2] | Monocyte-Derived Cutoff[3] |
| C4a Fold Increase (n = 32) | 0.0002 | 0.0002 |
| C5a Fold Increase (n = 32) | 0.0037 | 0.0037 |
| SC5b9 Fold Increase (n = 32) | <0.0001 | <0.0001 |
| IL-8 Fold Increase (n = 129) | 0.0006 | 0.0008 |
| Neutrophil Binding (n = 143) | <0.0001 | <0.0001 |
| Neutrophil CR1 Fold Increase (n = 32) | 0.2585 | 0.2085 |
| Neutrophil CR3 Fold Increase (n = 40) | 0.0249 | 0.0249 |
| Neutrophil CD88 Fold Decrease (n = 32) | 0.0074 | 0.0074 |
| Neutrophil CD62L Fold Decrease (n = 32) | 0.0058 | 0.0058 |
| Monocyte Binding (n = 143) | <0.0001 | <0.0001 |
| Monocyte CR1 Fold Increase (n = 36) | 0.0023 | 0.0028 |
| Monocyte CR3 Fold Increase (n = 37) | 0.0007 | 0.0007 |
| Monocyte CD88 Fold Decrease (n = 37) | 0.0801 | 0.0801 |

[1]p values
[2]Neutrophil IgG anti-β-glucan antibody concentration cutoff of 51 µg/ml and IgM cutoff of 118 µg/ml
[3]Monocyte IgG anti-β-glucan antibody concentration cutoff of 40 µg/ml and IgM cutoff of 126 µg/ml Biomarker cutoffs were then applied to patients in two clinical trials studying treatment of lung cancer that included IMPRIME PGG. In the first randomized, phase 2 study, 59 stage IV NSCLC patients received cetuximab, carboplatin, and paclitaxel without (Control) or with IMPRIME PGG 4 mg/kg on Days 1, 8 and 15 of each 3-week treatment cycle for the first 4 to 6 cycles. Maintenance treatment with cetuximab alone or in combination with IMPRIME PGG was continued until disease progression. Cutoffs at various points within the ranges established by healthy volunteer data and functional data above were investigated. The results are shown in Table 5.

TABLE 5

| IgG/IgM cutoffs | No. of Biomarker+ | Median Overall Survival (months) | | Survival Difference |
| --- | --- | --- | --- | --- |
| | | Biomarker+ | Biomarker− | |
| IgG: 51 µg/ml IgM: 118 µg/ml | 25 | 429 | 261 | 168 |
| IgG: 30 µg/ml IgM: 60 µg/ml | 41 | 289 | 162 | 127 |
| IgG: 40 µg/ml IgM: 80 µg/ml | 32 | 373 | 217.5 | 155.5 |
| IgG: 60 µg/ml IgM: 130 µg/ml | 23 | 378 | 244 | 134 |

Median Overall Survival (OS) was determined by investigators at the clinical trial sites. For some patients, biomarker status changes during the course of treatment. Therefore, biomarker positive status was given to patients that measured above the cutoff at either the first or second cycles.

As an example, using a cutoff of 51 µg/ml IgG anti-β-glucan antibody concentration, 118 µg/ml IgM anti-β-glucan antibody concentration 25 patients are biomarker positive. Biomarker-positive patients had a median overall survival of 429 days compared to 261 days for biomarker-negative patients. Thus, the survival difference between the two groups is 168 days, which is a significant difference. Of the examples given here, that cutoff produces the best separation in this clinical trial. The remaining example cutoffs produce smaller median overall survival differences between the two groups. However, in some cases, it may be ideal to have more patients treated by lowering the cutoff. And as discussed above, using ROC curve analysis, the specificity and sensitivity can be changed as needed for customizing patient separation.

In the second randomized, phase 2 study, 58 stage IV NSCLC patients received bevacizumab, carboplatin, and paclitaxel without (Control) or with IMPRIME PGG 4 mg/kg on a similar treatment cycle as the above study. Maintenance treatment with bevacizumab alone or in combination with IMPRIME PGG was continued until disease progression. Cutoffs at various points within the ranges established by healthy volunteer data and functional data above were investigated. The results are shown in Table 6.

TABLE 6

| IgG/IgM cutoffs | No. of Biomarker+ | Median Overall Survival (months) | | Survival Difference |
| --- | --- | --- | --- | --- |
| | | Biomarker+ | Biomarker− | |
| IgG: 60 µg/ml IgM: 100 µg/ml | 18 | 553 | 357 | 196 |
| IgG: 38 µg/ml IgM: 60 µg/ml | 26 | 474 | 437.5 | 36.5 |
| IgG: 80 µg/ml IgM: 120 µg/ml | 16 | 419 | 483 | −64 |
| IgG: 50 µg/ml IgM: 80 µg/ml | 25 | 474 | 437.5 | 36.6 |

For this clinical trial, the optimal cutoff occurs at 60 µg/ml IgG anti-β-glucan antibody concentration and 100 µg/ml IgM anti-β-glucan antibody concentration. As shown by the remaining examples, the cutoffs on either side of that cutoff quickly break down and do not provide practical differences.

Again, depending on the specificity and sensitivity desired (calculated by ROC curve analysis), one can select an appropriate cutoff to achieve stratification of patients that respond to IMPRIME PGG treatment without supplementation with anti-β-glucan antibodies.

Separation of patients based on biomarker status (high binder vs. low binder) can be accomplished using cutoffs within the ranges set forth above. Thus, biomarker status can be used as predictor of successful β-glucan immunotherapy.

As noted above, the biomarker status of some patients can change over the course of therapy. We therefore evaluated cutoff values for patients who exhibited biomarker-positive status after one cycle of therapy versus patients who exhibited biomarker-positive status after any cycle—after any one of C1/C2/C3—of therapy.

TABLE 7

Overall Survival of biomarker-positive patients exhibiting biomarker-positive status after one cycle of chemotherapy

| IgG/IgM Cutoffs (µg/ml) | Median OS (bevacizumab) | | Median OS (cetuximab) | |
|---|---|---|---|---|
| | BM+ | BM− | BM+ | BM− |
| 34/146 (235/330 RAU) | 401 | 471.5 | 283 | 275 |
| 35/100 (242/240 RAU) | 478 | 350 | 308 | 263 |
| 40/100 (276/240 RAU) | 482 | 343 | 373 | 247.5 |
| 45/100 (311/240 RAU) | 514 | 338.5 | 375.5 | 251 |
| 50/100 (345/240 RAU) | 514 | 338.5 | 375.5 | 251 |
| 55/100 (380/240 RAU) | 546 | 343 | 373 | 254.5 |
| 60/100 (414/240 RAU) | 553 | 338.5 | 308 | 266.5 |
| 35/110 (242/264 RAU) | 478 | 350 | 308 | 263 |
| 40/110 (276/264 RAU) | 482 | 343 | 378 | 247.5 |
| 45/110 (311/264 RAU) | 514 | 338.5 | 387.5 | 251 |
| 50/110 (345/264 RAU) | 482 | 343 | 387.5 | 251 |
| 55/110 (380/264 RAU) | 514 | 350 | 378 | 254.5 |
| 60/110 (414/264 RAU) | 546 | 343 | 308 | 266.5 |
| 35/120 (242/288 RAU) | 456 | 374.5 | 308 | 263 |
| 40/120 (276/288 RAU) | 474 | 357 | 378 | 247.5 |
| 45/120 (311/288 RAU) | 478 | 350 | 387.5 | 251 |
| 50/120 (345/288 RAU) | 474 | 357 | 387.5 | 251 |
| 55/120 (380/288 RAU) | 474 | 364 | 378 | 254.5 |
| 60/120 (414/288 RAU) | 478 | 360.5 | 308 | 266.5 |

As an example, using a cutoff of 60 µg/ml IgG anti-β-glucan antibody concentration, 100 µg/ml IgM anti-β-glucan antibody concentration to separate biomarker-positive from biomarker-negative patients, biomarker-positive patients receiving bevacizumab therapy had a median overall survival of more than 200 days more than biomarker-negative patients using the same cutoff values. Similarly, using a cutoff of 45 µg/ml IgG anti-β-glucan antibody concentration, 110 µg/ml IgM anti-β-glucan antibody concentration, biomarker-positive patients receiving cetuximab therapy had a median overall survival of more than 130 days more than biomarker-negative patients using the same cutoff values. As described above with respect to the data presented in Table 5 and Table 6, one can select an appropriate cutoff value for a desired combination of specificity and sensitivity, as needed for customizing patient separation, using ROC curve analysis.

TABLE 8

Overall Survival of biomarker-positive patients exhibiting biomarker-positive status after any cycle of chemotherapy

| IgG/IgM Cutoffs (µg/ml) | Median OS (bevacizumab) | | Median OS (cetuximab) | |
|---|---|---|---|---|
| | BM+ | BM− | BM+ | BM− |
| 34/146 (235/330 RAU) | 438 | 551 | 308 | 244 |
| 35/100 (242/240 RAU) | 478 | 499 | 298.5 | 244 |

TABLE 8-continued

Overall Survival of biomarker-positive patients exhibiting biomarker-positive status after any cycle of chemotherapy

| IgG/IgM Cutoffs (µg/ml) | Median OS (bevacizumab) | | Median OS (cetuximab) | |
|---|---|---|---|---|
| | BM+ | BM− | BM+ | BM− |
| 40/100 (276/240 RAU) | 482 | 483 | 328 | 217.5 |
| 45/100 (311/240 RAU) | 514 | 437.5 | 378 | 244 |
| 50/100 (345/240 RAU) | 514 | 437.5 | 378 | 244 |
| 55/100 (380/240 RAU) | 514 | 437.5 | 375.5 | 244 |
| 60/100 (414/240 RAU) | 546 | 392 | 373 | 247.5 |
| 35/110 (242/264 RAU) | 478 | 499 | 308 | 244 |
| 40/110 (276/264 RAU) | 482 | 483 | 328 | 217.5 |
| 45/110 (311/264 RAU) | 514 | 437.5 | 397 | 244 |
| 50/110 (345/264 RAU) | 482 | 483 | 397 | 244 |
| 55/110 (380/264 RAU) | 482 | 483 | 387.5 | 244 |
| 60/110 (414/264 RAU) | 514 | 437.5 | 378 | 247.5 |
| 35/120 (242/288 RAU) | 456 | 533 | 308 | 244 |
| 40/120 (276/288 RAU) | 474 | 515 | 328 | 217.5 |
| 45/120 (311/288 RAU) | 478 | 499 | 397 | 244 |
| 50/120 (345/288 RAU) | 474 | 515 | 397 | 244 |
| 55/120 (380/288 RAU) | 456 | 525.5 | 387.5 | 244 |
| 60/120 (414/288 RAU) | 474 | 515 | 378 | 247.5 |

Here again, one can select an appropriate IgG and IgM cutoff value to maximize survival of biomarker-positive patients. For example, using a cutoff of 60 µg/ml IgG anti-β-glucan antibody concentration, 100 µg/ml IgM anti-β-glucan antibody concentration, biomarker-positive patients receiving bevacizumab therapy had a median overall survival of more than 150 days more than biomarker-negative patients using the same cutoff values. Using a cutoff either 45 µs/ml or 50 µs/ml IgG anti-β-glucan antibody concentration, and either 110 µg/ml or 120 µg/ml IgM anti-β-glucan antibody concentration, biomarker-positive patients receiving bevacizumab therapy had a median overall survival of more than 150 days more than biomarker-negative patients using the same cutoff values.

In some clinical situations, however, overall survival may not necessarily be the most relevant clinical endpoint. In some cases, overall response rate (ORR) may be more relevant. As used herein, "overall response rate" refers to the percentage of patients that exhibit a measurable reduction in the size and/or proliferation of cancer after treatment. The data in Table 9 demonstrate that IgG and IgM cutoff values may be determined using ORR as the clinical endpoint. Table 9 reports combined data from the bevacizumab and cetuximab studies described above, reflecting mean overall survival and overall response rate as endpoints.

TABLE 9

| IgG/IgM Cutoffs (µg/ml) | Median OS | | | % ORR | | |
|---|---|---|---|---|---|---|
| | Bio+ | Bio− | Diff. | Bio+ | Bio− | Diff. |
| 35/100 | 368.5 | 294 | 74.5 | 57.14% | 40.38% | 16.76% |
| 40/100 | 387.5 | 286 | 101.5 | 59.57% | 38.89% | 20.69% |
| 45/100 | 438 | 283.5 | 154.5 | 63.41% | 38.33% | 25.08% |
| 50/100 | 438 | 283.5 | 154.5 | 63.41% | 38.33% | 25.08% |
| 55/100 | 418 | 286 | 132 | 65.00% | 37.70% | 27.30% |
| 60/100 | 446 | 286 | 160 | 63.16% | 39.68% | 23.48% |
| 65/100 | 425.5 | 292 | 133.5 | 61.11% | 41.54% | 19.57% |
| 35/110 | 373 | 293 | 80 | 57.14% | 40.38% | 16.76% |
| 40/110 | 397.5 | 286 | 111.5 | 58.70% | 40.00% | 18.70% |
| 45/110 | 454 | 283.5 | 170.5 | 62.50% | 39.34% | 23.16% |
| 50/110 | 446 | 286 | 160 | 61.54% | 40.32% | 21.22% |
| 55/110 | 438 | 289 | 149 | 63.16% | 39.68% | 23.48% |
| 60/110 | 454 | 289 | 165 | 61.11% | 41.54% | 19.57% |
| 65/110 | 454 | 293 | 161 | 58.82% | 43.28% | 15.54% |

TABLE 9-continued

| IgG/IgM Cutoffs | Median OS | | | % ORR | | |
|---|---|---|---|---|---|---|
| (µg/ml) | Bio+ | Bio− | Diff. | Bio+ | Bio− | Diff. |
| 35/120 | 364 | 305 | 59 | 57.45% | 40.74% | 16.71% |
| 40/120 | 387.5 | 292 | 95.5 | 59.09% | 40.35% | 18.74% |
| 45/120 | 438 | 289 | 149 | 63.16% | 39.68% | 23.48% |
| 50/120 | 418 | 292 | 126 | 62.16% | 40.63% | 21.54% |
| 55/120 | 397.5 | 294 | 103.5 | 65.71% | 39.39% | 26.32% |
| 60/120 | 417.5 | 294 | 123.5 | 63.64% | 41.18% | 22.46% |
| 65/120 | 387.5 | 316 | 71.5 | 61.29% | 42.86% | 18.43% |

Table 9 shows that the IgG/IgM cutoff values most effective for separating biomarker-positive from biomarker-negative patients may differ somewhat depending upon whether one uses overall survival or overall response rate as the clinical endpoint for making the separation. Thus, regardless of the clinical endpoint that is most relevant for the treatment of a given biomarker-positive patient, the methods described herein can provide IgG/IgM cutoff values for identifying biomarker-positive patients.

Once we established that biomarker status could be used as a predictor of successful β-glucan immunotherapy, we then looked at whether IgG subclasses played a role. IMPRIME PGG is a carbohydrate, and human IgG responses to carbohydrate antigens are primarily restricted to the $IgG_2$ subclass. $IgG_2$ is a poor complement activator and activates the classical pathway of complement activation only at antigen-antibody equivalence or when antibody is in excess. IMPRIME PGG has been shown to activate complement (C4a, C5a, SC5b9), but it does not cause cell lysis due to MAC formation on the cell surface. In addition, IMPRIME PGG, in the majority of the donors exhibits bell-shaped concentration—response curves. Binding, complement activation, and IL-8 production are optimal at 10 or 25 µg/ml but lower at 100 µg/ml. In some cases, this may be due to antigen-antibody being at equivalence or antibody being in excess at 10 µg/ml or 25 µg/ml, while the antigen is in excess at 100 µg/ml.

Figure 29:
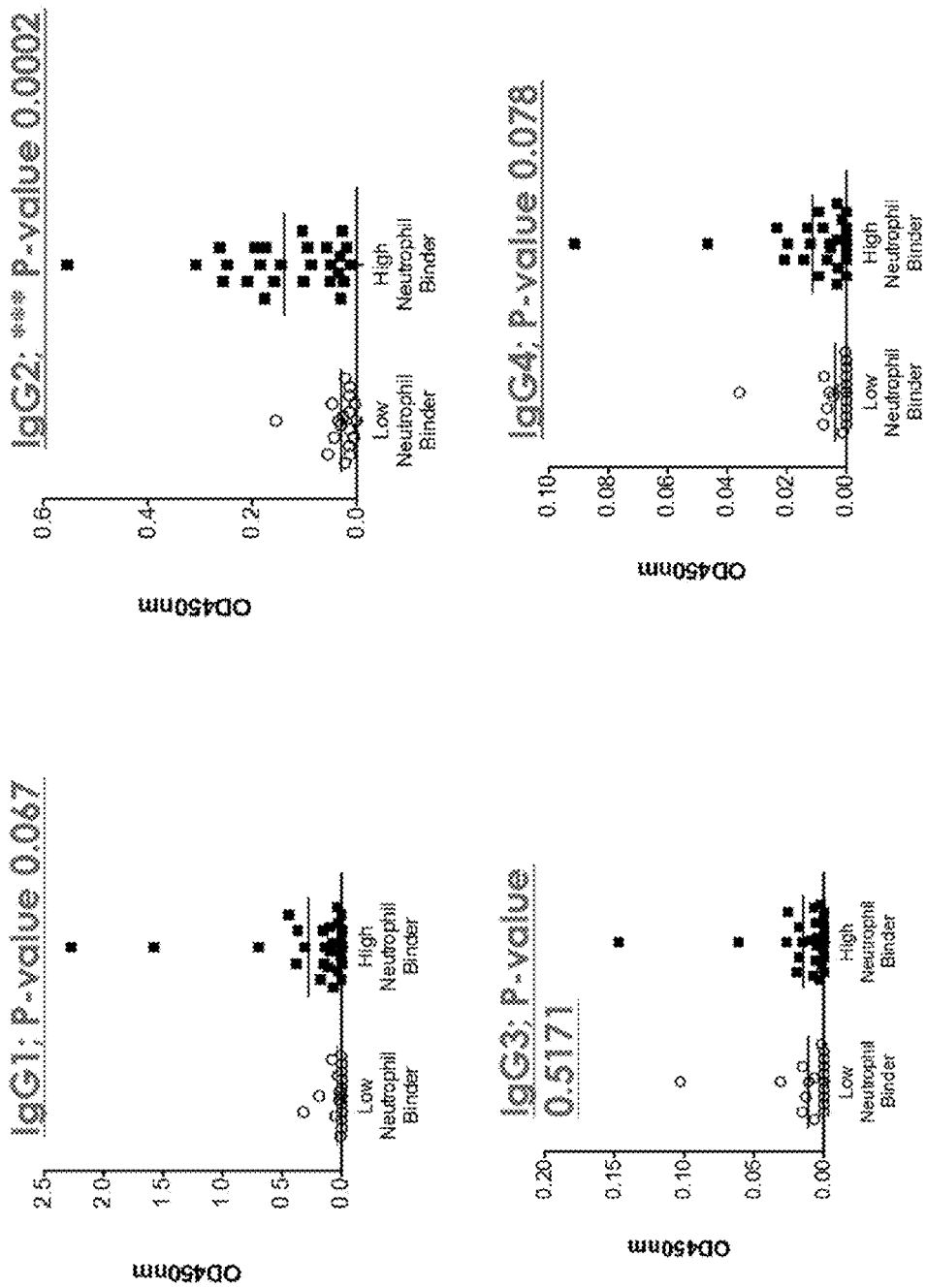
FIG. 29. IgG anti-β-glucan antibody subclass neutrophil binding based on high vs. low binder status.
Figure 30:
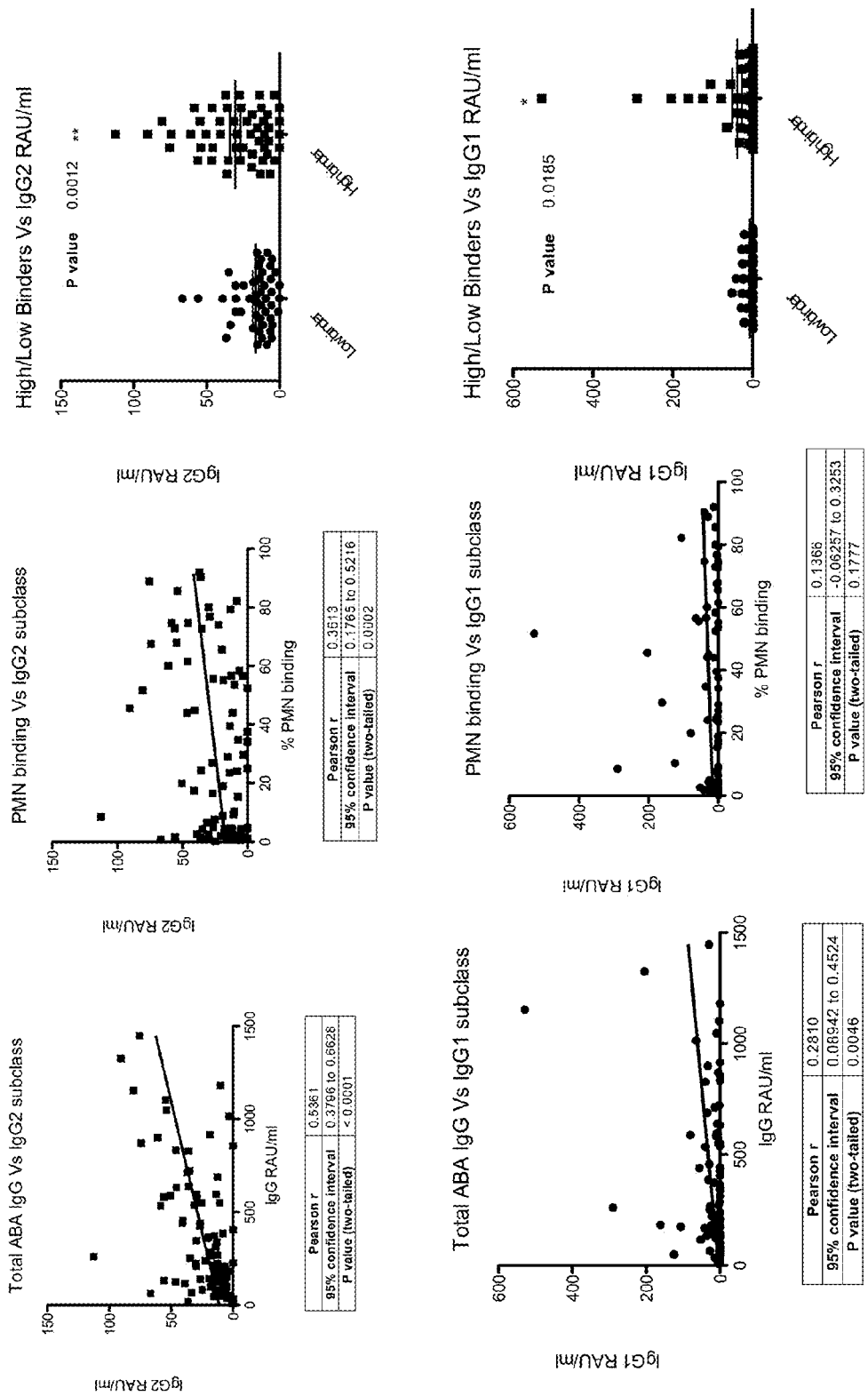
FIG. 30. IgG anti-β-glucan antibody subclass neutrophil binding.

To understand IgG subclasses as they relate to IgG anti-β-glucan antibodies, neutrophil binding was performed using secondary antibodies specific to each subclass of IgG anti-β-glucan antibodies. First, IgG subclasses from high binder and low binder serums were tested for binding to neutrophils. The results are shown in FIG. 29. As is evident from the results, $IgG_2$ subclass showed the strongest correlation to biomarker status. This finding was verified in the plots generated in FIG. 30. Neutrophil binding of $IgG_2$ anti-β-glucan antibodies from high binder serum produced a much stronger correlation than with $IgG_1$.

Therefore, in another embodiment, $IgG_2$ anti-β-glucan antibodies may be used as the predictive biomarker for IMPRIME PGG immunotherapy. In addition, for patients that are low binders, administration of $IgG_2$ anti-β-glucan may be used to improve their response to IMPRIME PGG immunotherapy.

Figure 31:
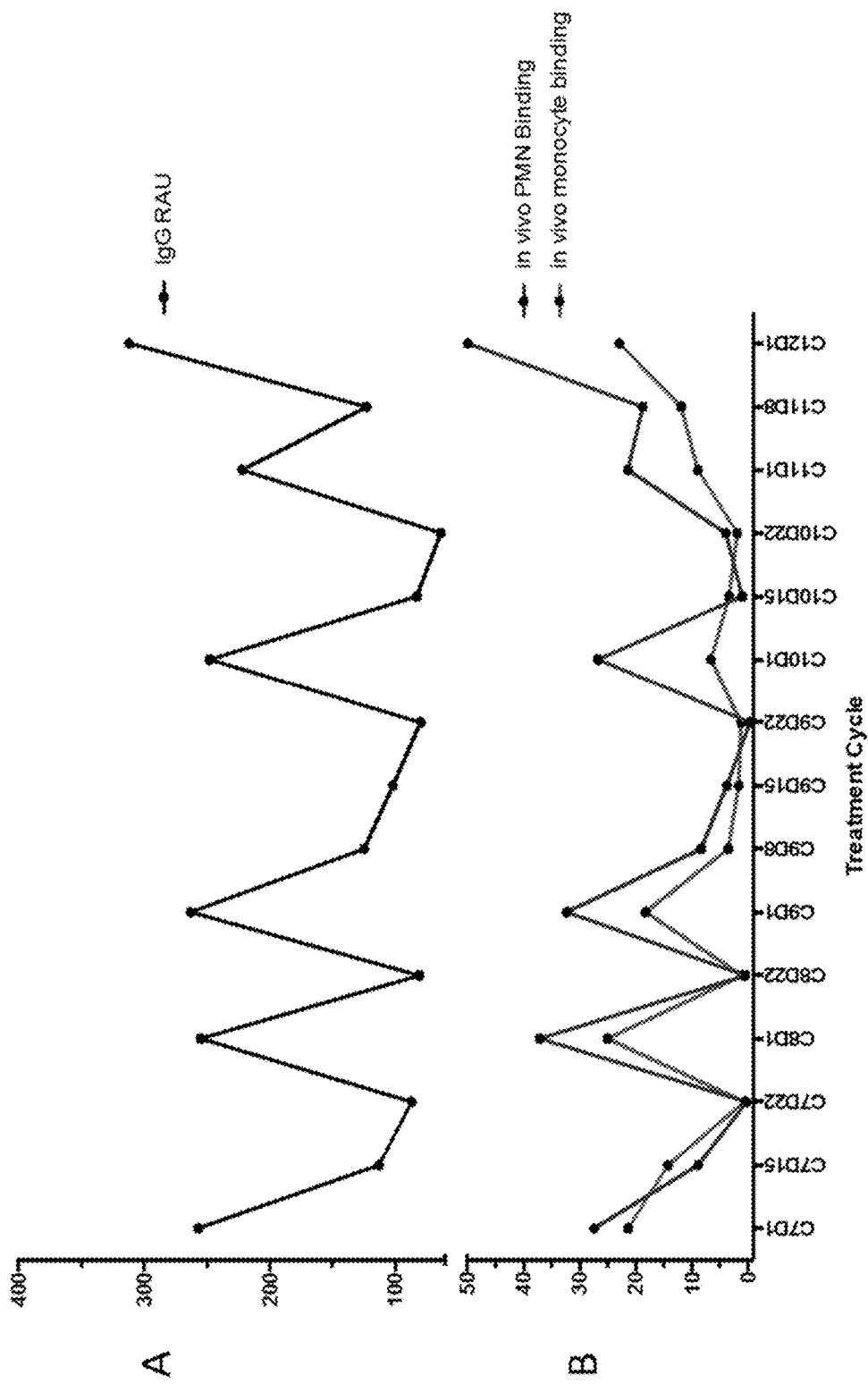
FIG. 31. Results of in vivo infusion of intravenous immunoglobulin (IVIG) to increase anti-β glucan antibody for IMPRIME PGG treatment of low binder patient. (A) IgG RAU; (B) PMN binding and monocyte binding; (C) C5a fold increase.
Figure 31:
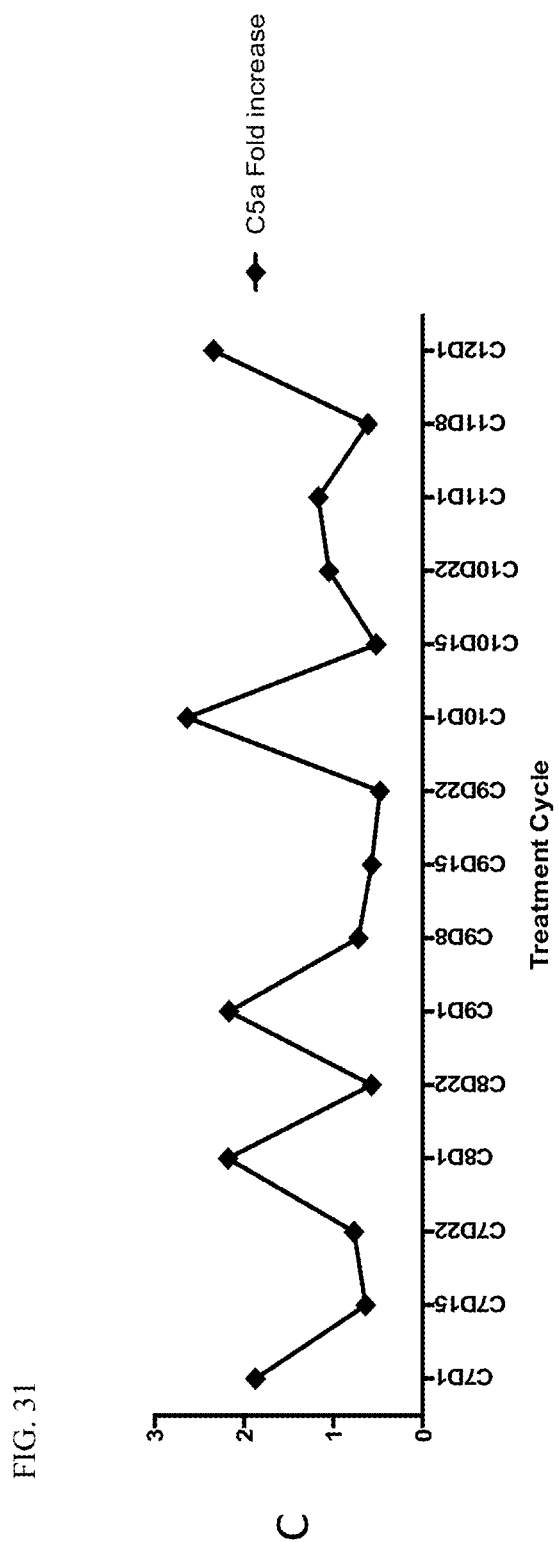

Lastly, it was shown that in vivo infusion of intravenous immunoglobulin (IVIG) increases anti-β-glucan antibody levels and improves response to IMPRIME PGG treatment. A 54-year old patient undergoing combination treatment of weekly infusions of cetuximab and IMPRIME PGG for colorectal adenocarcinoma had low anti-β-glucan antibody levels measured in pre-treatment serum samples. In order to increase the patient's anti-β-glucan antibody levels, IVIG (1 g/kg) was infused on the first day of a 28-day treatment cycle starting with cycle 7 and continuing until cycle 12. As shown in FIG. 31A, post treatment serum samples were analyzed for IgG anti-β-glucan antibody levels in RAU/ml by ELISA. Addition of IVIG increased the anti-β-glucan antibody concentration in the Day 1 sample of each cycle and then declined to baseline levels during the remaining weeks in each cycle. In FIG. 31B, in vivo binding of IMPRIME PGG binding to PMNs and monocytes was analyzed by FACS and calculated by the increase of IMPRIME PGG+ PMNs or monocytes in a post-IMPRIME PGG dose whole blood sample in comparison to a pre-dose sample. Binding varied with the level of anti-β-glucan antibody concentration measured with the highest binding for both PMNs and monocytes on days where the patient received an infusion of IVIG. In FIG. 31C, complement activation was measured by the fold increase of C5a as measured by ELISA in a post-IMPRIME PGG dose serum in comparison to a pre-dose sample. A two-fold increase in C5a level was only observed in patient samples corresponding with IVIG infusion.

The method described herein can identify individuals who are most likely to benefit from a therapeutic regimen that includes administration of β-glucan such as, for example, IMPRIME PGG. Thus, the assay can allow medical professionals to better tailor therapeutic treatments to an individual based, at least in part, on the subject's likelihood of responding to therapy that includes β-glucan. The assay may be used to screen individuals for inclusion in clinical studies to better define various subject populations.

The term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Costar universal binding plates were coated with 50 µL per well with IMPRIME PGG (Biothera, Eagan, Minn.) at 1 µg/mL in purified water and incubated at 37° C. for 30 minutes. The coated plate was then exposed to high intensity ultraviolet light at >1500 µW/cm$^2$ for 5 minutes at room temperature and placed in a 50° C. forced air oven until dry before a second exposure to ultraviolet light for five minutes at room temperature. The plate was then blocked with 0.5% solution of bovine serum albumin (BSA) for greater than 30 minutes before washing with wash buffer (phosphate buffered saline [PBS] with 0.05% Tween-20). Each assay run included two assay plates. Each plate included a calibration curve made by serially diluting the reference human serum. The plates also included four test serum samples diluted identically as the reference serum. The dilution series for the calibration curve and the serum samples started with a 1:400 dilution and continued with serial 1:2 dilutions to the lowest dilution of 1:51,200. The dilutions were made in wash buffer. A dilution of 1:50 of the reference serum was used as the highest anchor point on the curve. Each dilution of the reference and serum samples was evaluated in replicate wells on each of the two plates.

The samples were incubated on the assay plate at room temperature for 90 minutes to permit human IgG to bind to the plate-bound IMPRIME PGG. Following incubation, the wells were washed with wash buffer and an enzyme labeled secondary antibody (horseradish peroxidase conjugated affinity purified goat anti-human IgG, Fc gamma specific antibody) was incubated in the wells to bind with human IgG bound to IMPRIME PGG antigen. The secondary antibody was allowed to incubate for 90 minutes before washing with wash buffer. After the wash buffer was removed from the wells, a peroxidase substrate was incubated in the wells and color development was quenched with ~1M phosphoric acid at 5 minutes color development. The optical density at 450 nm was measured using a microtiter plate reader and means from replicate wells calculated.

The results were computed in two ways:

1) Titer: The titer was determined as the greatest dilution factor of sample with an optical density reading greater than or equal to 0.1 OD.

2) RAU—An arbitrary value of 160 was assigned to the reference serum (160 Relative Antibody Units (RAU/mL). Thus a 1:400 dilution in the assay method results in a value of 400 mRAU/mL as the highest point on the calibration curve. The dilution values and the corresponding RAU values are stated in Table 10.

TABLE 10

| Dilution | Mean OD | Calculated Conc. (mRAU/ml) | Calc. Conc. × Dil | Divide by 1000 = RAU/ml |
|---|---|---|---|---|
| 400 | 1.577 | 404.6 | | |
| 800 | 1.493 | 322.2 | 257749 | 258 |
| 1600 | 1.369 | 239.3 | 382912 | 383 |
| 3200 | 1.031 | 119.9 | 383683 | 384 |
| 6400 | 0.715 | 64.3 | 411398 | 411 |
| 12800 | 0.393 | 29.5 | 378022 | 378 |
| 25600 | 0.204 | 14.7 | 377574 | 378 |
| 51200 | 0.105 | 8.0 | | |

RAU values for samples and controls were calculated with a 4-parameter fit using the reference human serum dilution series as the calibration curve. The concentration in mRAU for each sample dilution that falls within the linear portion of the calibration curve was computed by interpolation from the calibration curve, followed by correction for dilution. Subsequently, an average concentration of each sample was arrived at from those back calculated multiple dilutions.

Results are shown in FIG. 1A.

Example 2

Figure 22:
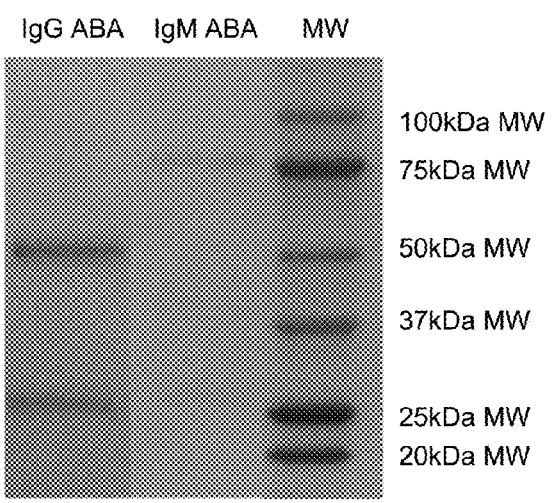
FIG. 22. SDS-PAGE (4-20% under reducing conditions) of purified "gold reference" IgG and IgM anti-β-glucan antibody stained with Coomassie Blue. Protein standards, with molecular weight (MW) expressed in kilodaltons (kDa), are shown in Lane 3.

IgG and IgM anti-β-glucan antibody "gold reference standards" were purified from commercially available, 95% pure total IgG and IgM fractions derived from pooled normal human plasma (Athens Research and Technology, Athens, Ga.). The IgG and IgM fractions were passed over IMPRIME PGG affinity columns, concentrated, and characterized using sodium dodecyl sulfate polyacrylamide gel electrophoresis (SDS-PAGE) for purity. See FIG. 22. Serial dilutions of the "gold reference standards" were used to generate calibration curves by the method described below for generating standard curves.

Assay working reference standards were prepared from pooled normal human serum with anti-β-glucan concentrations determined by calibration against the "gold reference standards." Assay controls were prepared from normal human serum from selected individual subjects with anti-β-glucan concentrations near defined locations on the working standard curves.

MAXISORP flat bottom 96-well plates (Thrmo Fisher Scientific, Waltham, Mass.) are coated with 100 μL per well of IMPRIME PGG at 3 μg/mL in D-PBS (Corning Inc., Tewksbury, Mass.). The plates are covered, placed in a tightly sealed zip closure plastic bag and incubated at 4° C. for a minimum of 15 hours and a maximum of 24 hours. The coated plates are then removed from refrigeration, aspirated and washed three times with wash buffer (0.05% Polysorbate 20 (Alfa Aesar, Ward Hill, Mass.) in PBS). Following the final aspiration, each coated plate is completely wrapped in a paper towel and tapped hard three times on a cushion of paper towels to remove the remaining liquid. The plate is then blocked with 250 μl per well of StabilCoat Immunoassay Stabilizer (SurModics, Inc., Eden Prairie, Minn.) for 1 to 3 hours on the bench top. After blocking, the plates are aspirated to remove the contents and wrapped in a paper towel. The tapping procedure to remove the remaining liquid, as described above, is repeated. The plates are uncovered and allowed to dry for a minimum of 45 minutes and up to three hours on the bench top.

Each assay included a working standard curve made by serially diluting a working reference sample. The dilution series of the working reference samples are shown in Tables 11 and 12. The assay also included control and test samples diluted 1:20, 1:400 and 1:1600. The dilutions were made in wash buffer. Each dilution of the reference and serum samples was evaluated in triplicate.

The samples were incubated on the assay plate at room temperature for 45 minutes on an orbital shaker with an orbital diameter of 2 mm set to 310 rpm to permit human IgG and/or IgM to bind to the plate-bound IMPRIME PGG. Following incubation, the wells were washed with wash buffer and an enzyme labeled secondary antibody (horseradish peroxidase conjugated affinity purified goat anti-human IgG or IgM, Fc gamma specific antibody) was incubated in the wells to bind with human IgG or IgM bound to IMPRIME PGG antigen. The secondary antibody was allowed to incubate for 45 minutes before washing with wash buffer. After the wash buffer was removed from the wells, a peroxidase substrate was incubated in the wells and color development was quenched with ~1M phosphoric acid at five minutes color development. The optical density at 450 nm was measured using a microtiter plate reader and means from replicate wells calculated.

IgG and IgM anti-β-glucan antibody concentrations (μg/ml) were determined by correlating the sample absorbance against the working standard curve generated from the working reference sample dilutions. The dilution values and the corresponding concentrations for a calibration curve are stated in Tables 11 and 12.

TABLE 11

IgG Dilutions for Standard Curve

| Dilution | Mean OD | Mean Calculated Conc. (ng/ml) |
|---|---|---|
| 1:10 | 2.859 | 42073.3 |
| 1:100 | 2.626 | 191.0 |
| 1:400 | 2.214 | 58.2 |
| 1:800 | 1.773 | 29.1 |
| 1:1600 | 1.161 | 13.7 |
| 1:3200 | 0.674 | 7.1 |
| 1:12800 | 0.202 | 2.0 |

TABLE 12

IgM Dilutions for Standard Curve

| Dilution | Mean OD | Mean Calculated Conc. (ng/ml) |
|---|---|---|
| 1:6.26 | 2.642 | 11176.3 |
| 1:50.08 | 2.133 | 1354.7 |
| 1:100.17 | 1.706 | 664.4 |
| 1:200.33 | 1.227 | 338.5 |
| 1:801.38 | 0.454 | 83.7 |
| 1:3204.76 | 0.158 | 20.8 |
| 1:12819 | 0.079 | 5.2 |

Figure 1B:
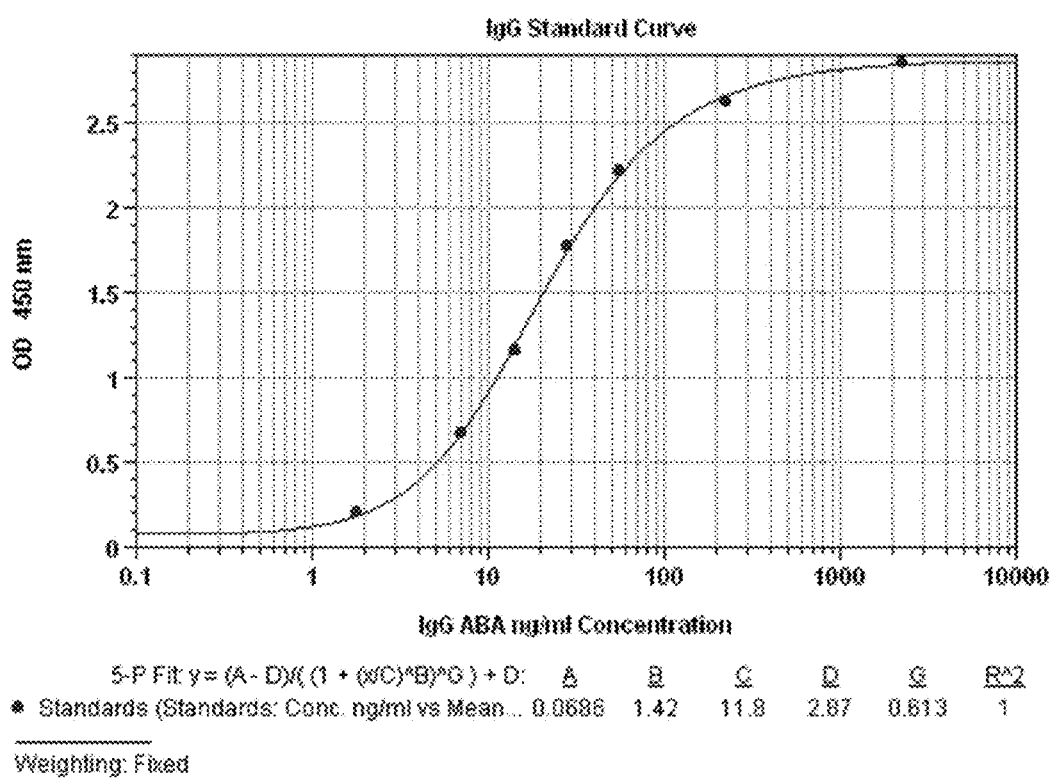
FIG. 1B. IgG anti-β-glucan antibody concentration working standard curve.
Figure 1C:
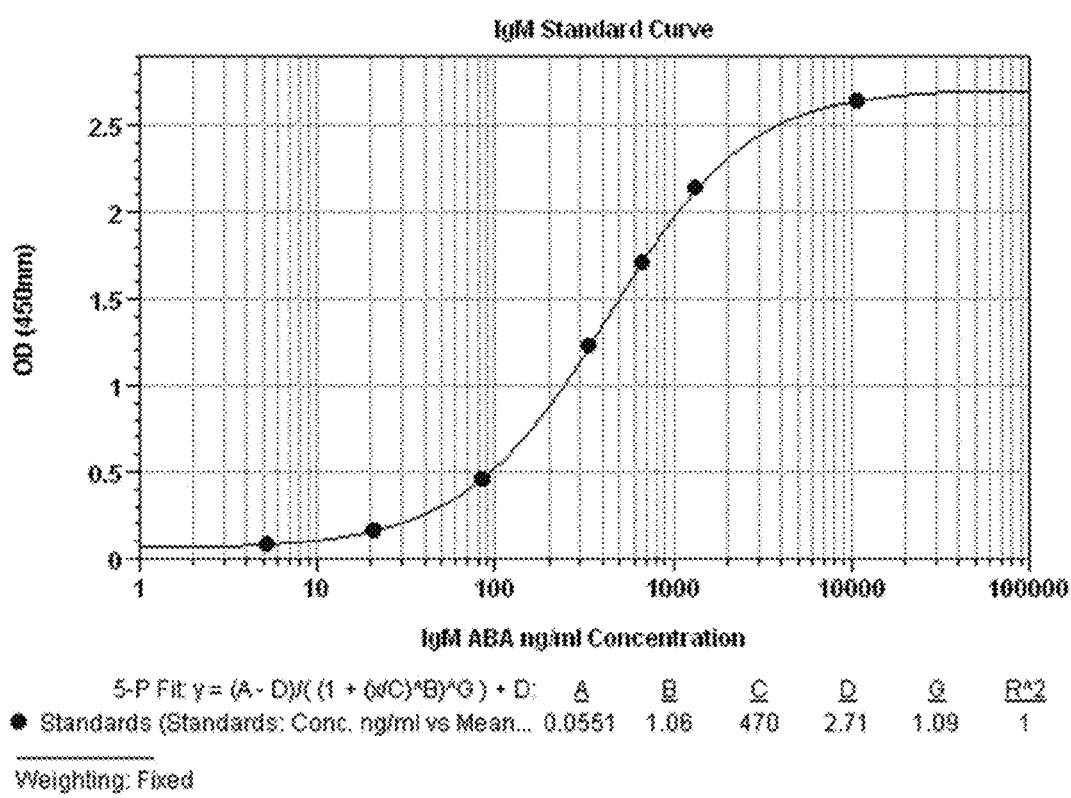
FIG. 1C. IgM anti-β-glucan antibody concentration working standard curve.

Standard curves derived from the data of Tables 11 and 12 are shown in FIGS. 1B and 1C, respectively. Once the antibody concentration of the test samples is determined by the standard curve, the concentrations can be converted to µg/ml by multiplying the mean calculated concentration by the dilution factor and then divided by 1000.

Example 3

Whole blood (WB) was collected from healthy volunteers in heparin containing tubes (BD VACUTAINER sodium heparin tubes, Becton Dickinson, Franklin Lake, N.J.). The IVIG used in the study was Privigen, a 10% solution of human polyvalent human immunoglobulin at 100 mg/mL (CSL Behring, King of Prussia, Pa.). Samples were spiked with dilutions of IVIG in PBS to final concentrations of 2.5 mg/mL, 5 mg/mL, and 10 mg/mL along with a PBS only control. Aliquots of the IVIG spiked blood were then made for IgG RAU assays, and IMPRIME PGG induction of complement pathway activation, neutrophil binding (described below in Example 4), activation marker expression, and IL-8 production assays.

Aliquots of the IVIG spiked WB were incubated with IMPRIME PGG at 10 µg/mL or equivalent volume of citrate buffer (11 mM NaCitrate, 140 mM NaCL, pH 6.3) as a control for 30 minutes at 37° C. After incubation, cells were washed twice with PBS before adding 5 µL of BfD IV mouse anti-beta glucan IgM antibody per 100 µL of WB and incubating at room temperature for 15 minutes. The samples were then washed twice again with PBS and stained with an antibody cocktail containing antibodies for surface markers as well as an anti-mouse IgM for detection of BfD IV binding. Cells incubated 30 minutes at room temperature before adding 2 mL of FACS/Lyse (eBiosciences, San Diego, Calif.) and incubating at room temperature for 15 minutes. The cells were then washed two times with PBS before fixing with 1% paraformaldehyde and analyzing on LSRII flow cytometer. FACS data analyzed by FlowJo software.

Results are shown in FIGS. 2-7.

Example 4

Binding of IMPRIME PGG in WB and the detection of glucan binding on cell surface were performed essentially as described above in Example 2.

Results are shown in FIGS. 8-13, 23-30, 31A and 31B.

Example 5

Whole blood (WB) was collected from healthy volunteers in heparin containing tubes as described in Example 3. The tube was mixed well and stored on ice until ready to use. Aliquots of WB were incubated with IMPRIME PGG at a final concentration of 10 µg/mL or 100 µg/mL, or with equivalent volume of PBS or Citrate Buffer. Whole glucan particle (WGP) at 10 µg/mL was used as a positive control. Treated WB were incubated at 37° C. in a humidified 5% $CO_2$ incubator for 30 minutes or 120 minutes. Immediately at the end of each time point, WB was centrifuged at 2000×rpm (or 1150×g) for 10 minutes at 4° C. The supernatant (plasma) was collected, and transferred to a 1.5 mL eppendorf tube and kept on ice. The plasma was used the same day in complement modulation study as described in the following section or was frozen at −70° C. until ready to use.

Complement C4a Modulation Study.

The MicroVue C4a EIA kit (Quidel Corp., San Diego, Calif.) was used for the quantitation of C4a in plasma according to the vendor's instruction. In brief, Standards, Controls, and 1:20 diluted test specimens (untreated or various treated plasma preparations) were added to microassay wells pre-coated with a specific anti-C4a monoclonal antibody. After incubation at room temperature for 60 minutes, the plate was washed and a wash cycle. Horseradish peroxidase (HRP)-conjugated murine anti-human C4a monoclonal antibody was added to each test well and incubated for another 60 minutes at room temperature. Following incubation, the plate was washed and a wash cycle, before the addition of a chromogenic enzyme substrate TMB to initiate the enzymatic reaction. The plate was incubated at room temperature for 60 minutes and the enzyme reaction was subsequently quenched with the provided stop solution. The color intensity was measured spectrophotometrically at 450 nm. The concentration of C4a present in the test specimens were calculated from the standard curve generated with the provided standards, and analyzed using a 4-parameter regression analysis.

Figure 14:
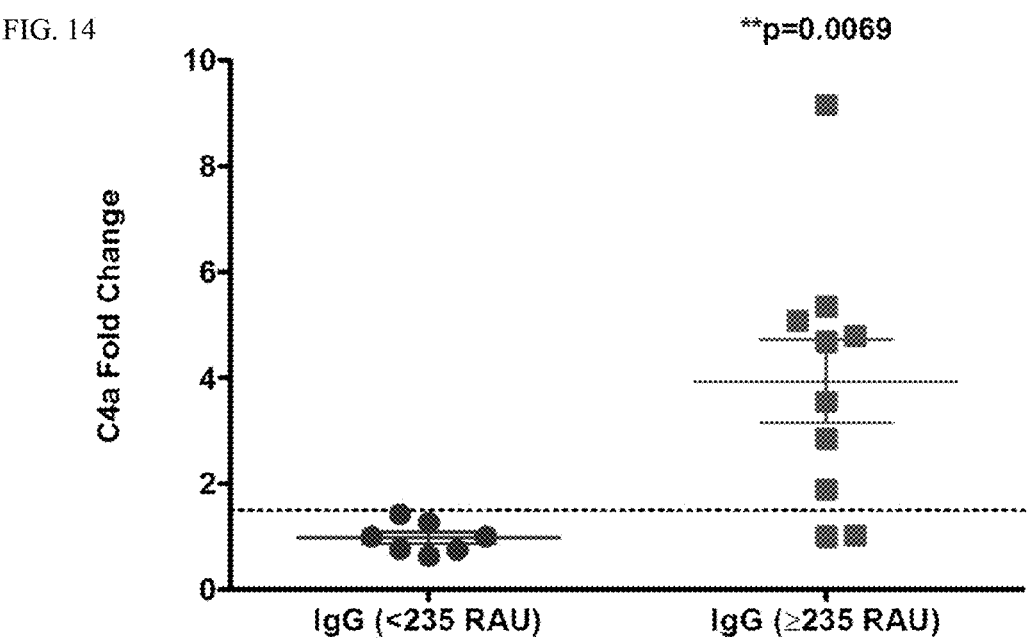
FIG. 14. Correlation of Anti-beta Glucan Antibody Levels and C4a Production in Whole Blood from Healthy Donors. The amount of C4a in WB cultures stimulated 30 minutes with IMPRIME PGG (10 µg/ml) from individual healthy donors are presented as fold change over citrate control in the Y axis. The mean fold change ±SEM are presented for each group in the X axis. 8/10 individuals (80%) with an IgG RAU of ≥235 and 0/7 individuals with an IgG RAU of <235 demonstrated a ≥1.5-fold C4a production with IMPRIME PGG, supporting a significant correlation between high RAU and greater complement activation (**p=0.0069).

Results are shown in FIG. 14.

Complement C5a Modulation Study.

The MicroVue C5a EIA kit (Quidel Corp., San Diego, Calif.) was used for the quantitation of C5a in plasma according to the vendor's instruction. In brief, Standards, Controls, and 1:60 diluted test specimens (untreated or various treated plasma preparations) were added to microassay wells pre-coated with a specific anti-C5a monoclonal antibody. After incubation at room temperature for 60 minutes, the plate was washed and a wash cycle. Horseradish peroxidase (HRP)-conjugated murine anti-human C5a monoclonal antibody was added to each test well and incubated for another 60 minutes at room temperature. Following incubation, the plate was washed and a wash cycle, before the addition of a chromogenic enzyme substrate TMB to initiate the enzymatic reaction. The plate was incubated at room temperature for 60 minutes and the enzyme reaction was subsequently quenched with the provided stop solution. The color intensity was measured spectrophotometrically at 450 nm. The concentration of C5a present in the test specimens were calculated from the standard curve generated with the provided standards, and analyzed using a 4-parameter regression analysis.

Figure 15:
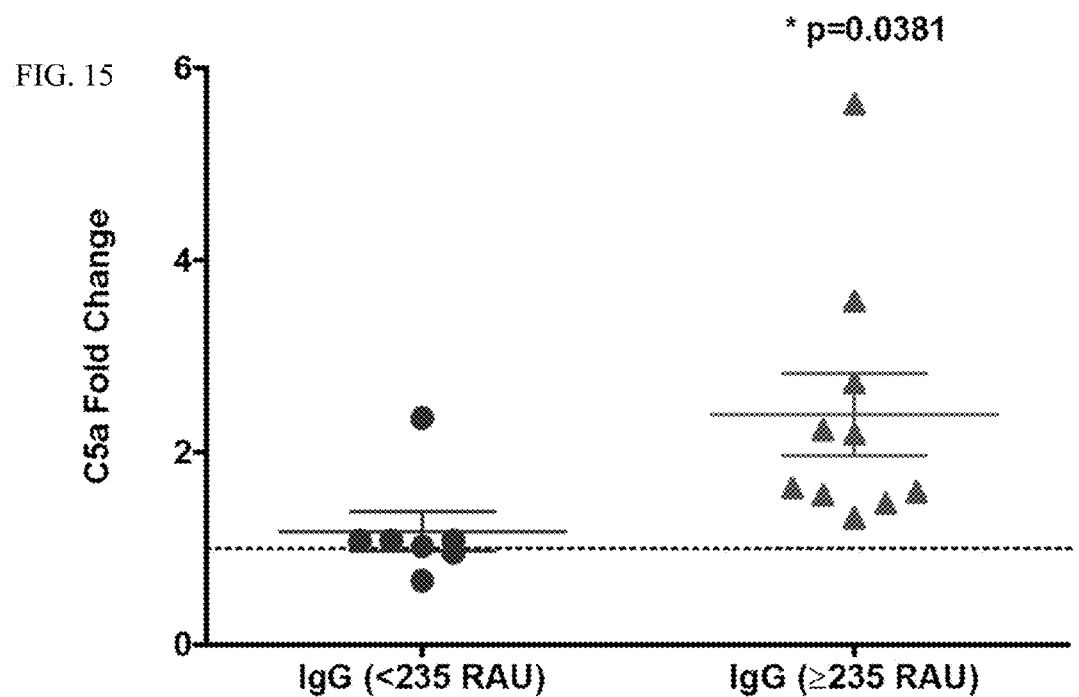
FIG. 15. Correlation of Anti-beta Glucan Antibody Levels and C5a Production in Whole Blood from Healthy Donors. The amount of C5a in WB cultures stimulated 30 minutes with IMPRIME PGG (10 µg/ml) from individual healthy donors are presented as fold change over citrate control in the Y axis. The mean fold change ±SEM are presented for each group in the X axis. 10/10 individuals with an IgG RAU of ≥235 and 1/7 individuals (14%) with an IgG RAU of <235 demonstrated a ≥1.5-fold C5a production with IMPRIME PGG, supporting a significant correlation between high RAU and greater complement activation (*p=0.0381).

Results are shown in FIG. 15 and FIG. 31C.

Sc5b-9 Modulation Study.

The MicroVue SC5b-9 Plus EIA kit (Quidel Corp., San Diego, Calif.) was used to measure the amount of the SC5b-9 complex present in plasma specimens according to the vendor's instruction. Briefly, Standards, Controls, and 1:20 diluted test specimens (untreated or various treated plasma preparations) were added to microassay wells pre-coated with a specific anti-SC5b-9 monoclonal antibody. The plate was incubated at room temperature for 60 minutes followed by five washes. The plate was then incubated at room temperature for 30 minutes with the provided SC5b-9 Plus Conjugate that contained a horseradish peroxidase-conjugated murine anti-human Ab specific for SC5b-9. The plate was then washed five times, incubated with a chromogenic enzyme substrate TMB for 60 minutes at room temperature to initiate the enzymatic reaction and subsequently quenched with the stop solution. $OD_{450}$ was measured. Results were calculated from the generated standard curve using linear regression analysis.

Figure 16:
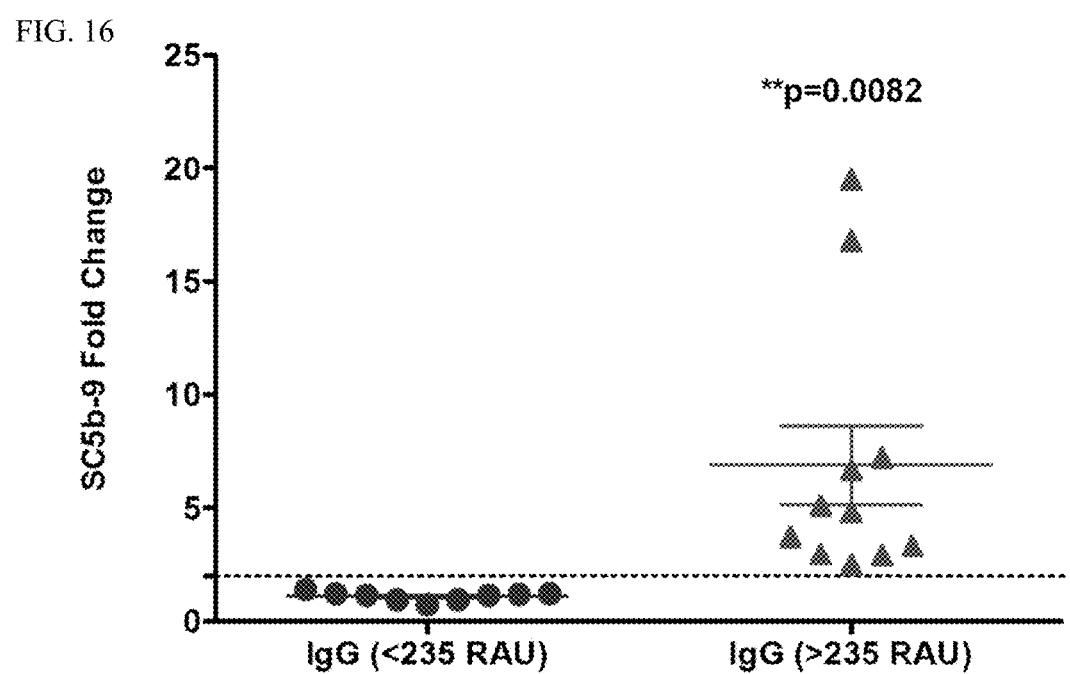
FIG. 16. Correlation of anti-beta glucan RAU levels and SC5b-9 production in whole blood from healthy donors. The amount of SC5b-9 in healthy donor whole blood cultures incubated 30 minutes with IMPRIME PGG (10 µg/ml). SC5b-9 levels (Y-axis) presented as fold change over citrate control satisfied by IgG RAU status (X axis). 11/11 (i.e., 100%) individuals with an IgG RAU of ≥235 versus 0/9 (i.e., 0%) individuals with an IgG RAU of <235 demonstrated a ≥2-fold SC5b-9 production, supporting a significant correlation between high RAU and greater complement activation (**p=0.0082).

Results are shown in FIG. 16.

Modulation of Cell Surface Complement Receptors.

Binding of IMPRIME PGG to WB was studied at 10 µg/mL and 100 µg/mL, and at both 30 minutes and 120 minutes. After binding, cells were washed twice with PBS and then incubated with CD88-APC, CD35-PE, and CD11b-PB (BioLegend) for 30 minutes at room temperature. RBC were lysed by incubating with 2 mL of FACS/Lyse (eBiosciences, San Diego, Calif.) at room temperature for 15 minutes. Cells were washed twice with PBS, fixed with 1% paraformaldehyde and analyzed on LSRII flow cytometer. FACS data analyzed by FlowJo software.

Figure 17:
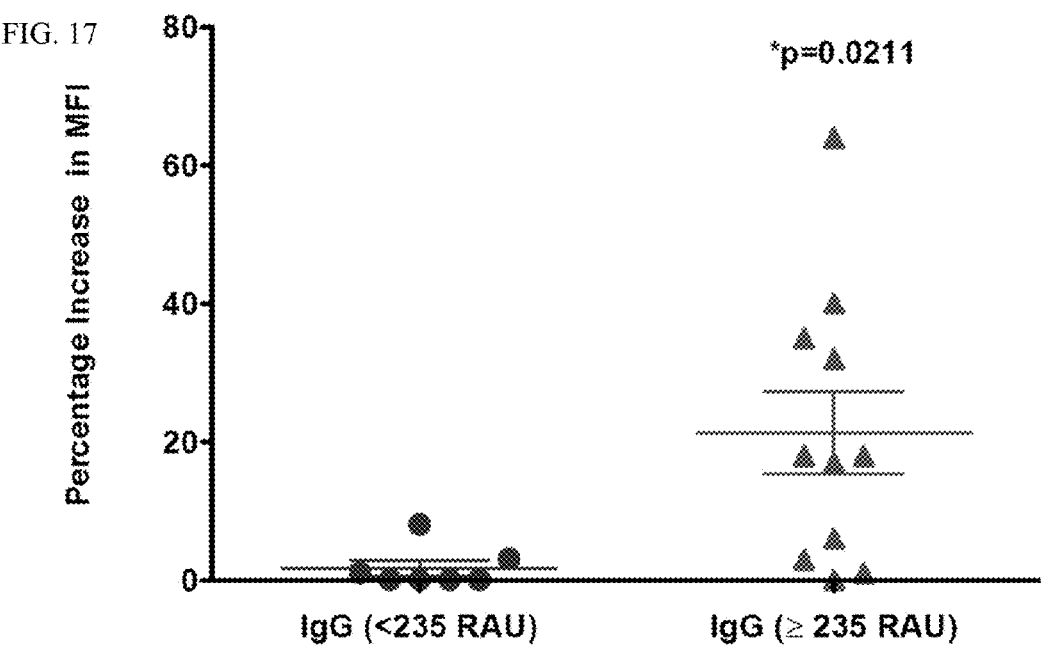
FIG. 17. Correlation of Anti-beta Glucan Antibody Levels and Increase in Surface Expression of CR3 in PMN of Whole Blood from Healthy Donors. Surface expression of CR3 on CD15+ neutrophils in WB cultures stimulated 30 minutes with IMPRIME PGG (10 µg/ml) from individual healthy donors are presented as MFI percentage change over citrate control in the Y axis. The mean MFI percentage change ±SEM are presented for each group in the X axis. In comparison to the individuals with an IgG RAU of <235 (N=7), neutrophils from individuals with an IgG RAU of ≥235 (N=11) demonstrated significant increase in surface CR3 levels (*p=0.0211).
Figure 18:
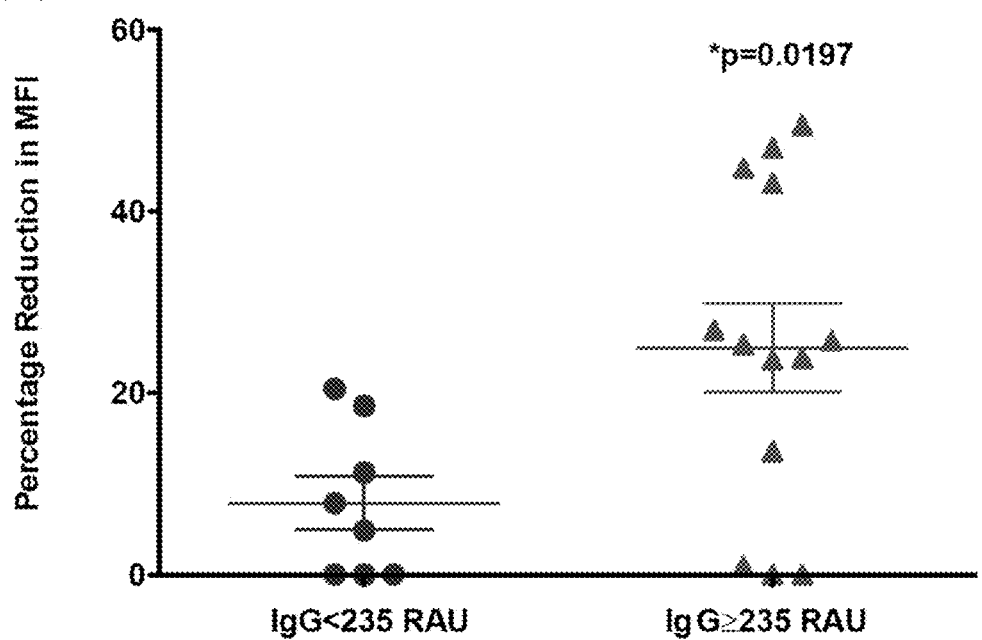
FIG. 18. Correlation of Anti-beta Glucan Antibody Levels and Reduction of CD88 Expression in PMN of Whole Blood from Healthy Donors. Surface expression of CD88 on CD15+ neutrophils in WB cultures stimulated 30 minutes with IMPRIME PGG (10 µg/ml) from individual healthy donors are presented as MFI percentage change over citrate control in the Y axis. The mean MEI percentage change ±SEM are presented for each group in the X axis. In comparison to the individuals with an IgG RAU of <235 (N=8), neutrophils from individuals with an IgG RAU of ≥235 (N=13) demonstrated significant reduction in surface CD88 levels (*p=0.0197).

Results are shown in FIG. 17 and FIG. 18.

Example 6

Binding of IMPRIME PGG to WB was studied at 10 µg/mL and 100 µg/mL, and at both 30 minutes and 120 minutes. After binding, cells were washed twice with PBS and then incubated with CD62L-PB (BioLegend) for 30 minutes at room temperature. RBC were lysed by incubating with 2 mL of FACS/Lyse (eBiosciences, San Diego, Calif.) at room temperature for 15 minutes. Cells were washed twice with PBS, fixed with 1% paraformaldehyde and analyzed on LSRII flow cytometer. FACS data analyzed by FlowJo software.

Figure 19:
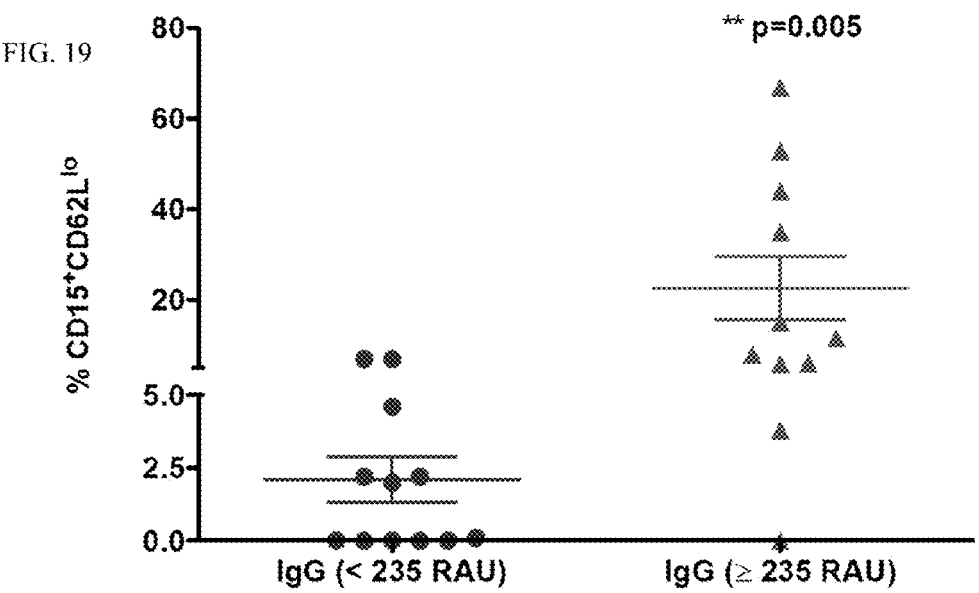
FIG. 19. Healthy donor whole blood was incubated with IMPRIME PGG (10 µg/ml) and surface expression of CD62L on CD15+ neutrophils assayed. The percent $CD15^+$ $CD62L^{lo}$ cells (individual and mean±SEM) is presented on the Y-axis stratified by RAU status on the X axis. Neutrophils from individuals with an IgG RAU of ≥235 demonstrated significant loss of CD62L expression (**p=0.005).

Results are shown in FIG. 19.

Example 7

Whole blood (WB) was collected from healthy volunteers in heparin containing tubes as described in Example 3. Aliquots of WB were incubated with IMPRIME PGG at final concentration of 10 µg/mL or 100 µg/mL, or treated with PBS or Citrate Buffer as a baseline control, or with 100 ng/mL of TLR4 agonist LPS (*E. coli* strain 0127:B8, Sigma, St. Louis, Mo.) as a positive control. The cultures were incubated at 37° C. in a humidified 5% $CO_2$ incubator. After 20-24 hours, the WB was centrifuged for 10 min at 1600× rpm, and the plasma supernatant was collected. Samples were stored in a 96-well Matrix storage plate (Matrix Technologies, Hudson, N.H.) at −80° C. until ready to use. The presence of IL-8 in the plasma samples of IMPRIME PGG-, or control-treated WB were determined by performing a Human CXCL8/IL-8 ELISA (R&D Systems, Catalog# D8000C, Minneapolis, Minn.) per the manufacturer's instructions.

Figure 20:
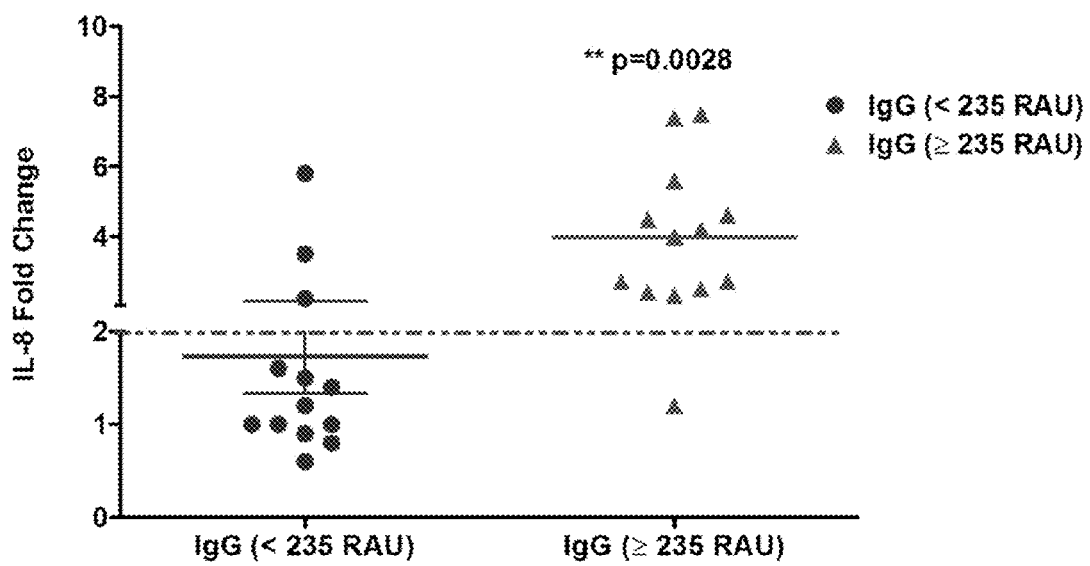
FIG. 20. Healthy donor whole blood was incubated overnight with IMPRIME PGG (10 µg/ml) then plasma IL-8 levels measured. IL-8 levels (Y-axis) presented as fold change over citrate control stratified by IgG RAU Status (X axis). 12/13 (i.e., 92%) individuals with an IgG RAU of ≥235 versus only 3/13 (i.e., 23%) individuals with an IgG RAU of <235 demonstrated a ≥2-fold IL-8 production with IMPRIME PGG, supporting a significant correlation between high RAU and greater IL-8 production (**p=0.0028).

Results are shown in FIG. 20.

Example 8

Sc5b-9 Modulation Study.

The MicroVue SC5b-9 Plus EIA kit (Quidel Corp., San Diego, Calif.) was used to measure the amount of the SC5b-9 complex present in plasma specimens according to the vendor's instruction. Briefly, Standards, Controls, and 1:20 diluted test specimens (untreated or various treated plasma preparations) were added to microassay wells pre-coated with a specific anti-SC5b-9 monoclonal antibody. The plate was incubated at room temperature for 60 minutes followed by five washes. The plate was then incubated at room temperature for 30 minutes with the provided SC5b-9 Plus Conjugate that contained a horseradish peroxidase-conjugated murine anti-human Ab specific for SC5b-9. The plate was then washed five times, incubated with a chromogenic enzyme substrate TMB for 60 minutes at room temperature to initiate the enzymatic reaction and subsequently quenched with the stop solution. $OD_{450}$ was measured.

Figure 21:
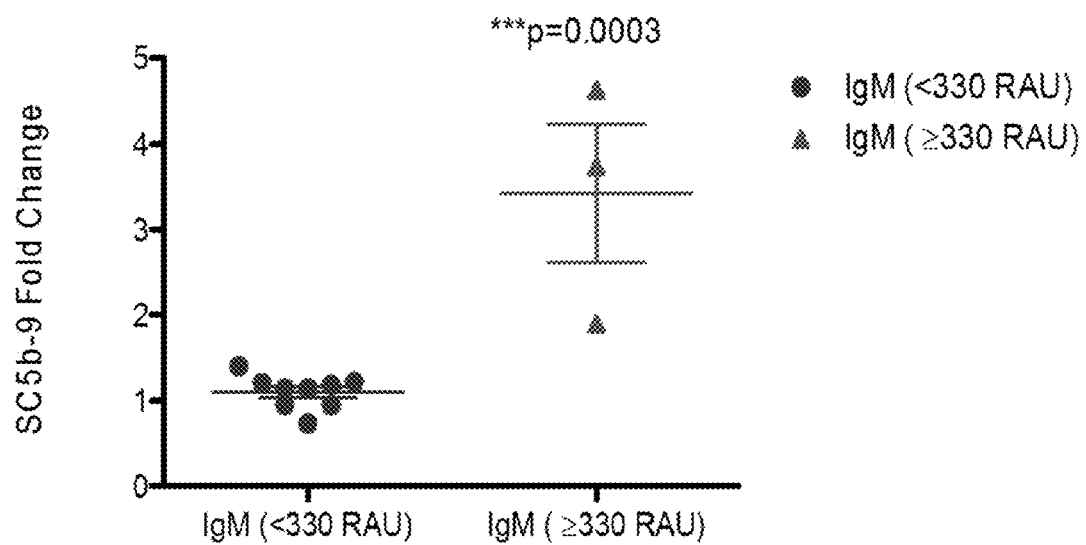
FIG. 21. Correlation of Anti-beta Glucan Antibody Levels and SC5b-9 Production in Whole Blood from Healthy Donors. The amount of SC5b-9 in WB cultures stimulated 30 minutes with IMPRIME PGG (10 µg/ml) from individual healthy donors are presented as fold change over citrate control in the Y axis. The mean fold change ±SEM are presented for each group in the X axis. In comparison to the individuals with an IgM RAU of <235 (N=9), neutrophils from individuals with an IgM RAU of ≥330 (N=3) demonstrated significant increase in SC5b-9 production (***p=0.0003).

Results were calculated from the generated standard curve using liner regression analysis. Results are shown in FIG. 21.

Example 9

ROC curve analysis was carried out using GraphPad Prism software. Results are shown in FIGS. 27 and 28.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method comprising:
    obtaining a biological sample from a subject;
    analyzing the sample for a biomarker anti-β-glucan antibody compared to a reference standard;
    computing a Relative Antibody Unit (RAU) value for anti-β-glucan antibody in the sample;
    identifying the subject having a RAU value greater than or equal to a predetermined RAU value for the biomarker anti-beta-glucan antibody, and therefore is biomarker positive for beta-glucan immunotherapy, wherein the predetermined RAU value is selected based on a correlation of specificity and sensitivity to at least one endpoint that stratifies biomarker-positive subjects and biomarker negative subjects; and
    administering β-glucan immunotherapy to the biomarker-positive subject.

2. The method of claim 1 wherein the biomarker anti-β-glucan antibody comprises IgG.

3. The method of claim 1 wherein the biomarker anti-β-glucan antibody comprises IgG and the predetermined RAU value is 200.

4. The method of claim 1 wherein the biomarker anti-β-glucan antibody comprises IgM.

5. The method of claim 1 wherein the biomarker anti-β-glucan antibody comprises IgM and the predetermined RAU value is 300.

6. The method of claim 1 wherein the β-glucan is derived from yeast.

7. The method of claim 1 wherein the β-glucan comprises a β-1,3/1,6 glucan.

8. The method of claim 1 wherein the β-glucan comprises β(1,6)-[poly-(1,3)-D-glucopyranosyl]-poly-β(1,3)-D-glucopyranose.

9. The method of claim 1 wherein the sample is analyzed for a biomarker anti-β-glucan antibody using an enzyme-linked immunosorbent assay (ELISA).

10. The method of claim 1 wherein the endpoint comprises clinical outcomes, binding to immune cells, activation of complement components, modulation of immune cell surface marker expression, or induction of cytokines.

11. A method comprising:
    obtaining a biological sample from a subject;
    analyzing the sample for a biomarker anti-β-glucan antibody compared to a reference standard;
    identifying the subject as having a RAU value greater than or equal to a predetermined RAU value for the biomarker anti-beta-glucan antibody, and therefore is biomarker positive for beta-glucan immunotherapy, wherein the the predetermined cutoff value is selected based on a correlation of specificity and sensitivity to at least one endpoint that stratifies biomarker-positive subjects and biomarker-negative subjects; and
    administering P-glucan immunotherapy to the biomarker-positive subject.

12. The method of claim 11 wherein the biomarker anti-β-glucan antibody comprises IgG.

13. The method of claim 11 wherein the biomarker anti-β-glucan antibody comprises IgM.

14. The method of claim 11 wherein the β-glucan is derived from yeast.

15. The method of claim 11 wherein the β-glucan comprises a β-1,3/1,6 glucan.

16. The method of claim 11 wherein the β-glucan comprises β(1,6)-[poly-(1,3)-D-glucopyranosyl]-poly-β(1,3)-D-glucopyranose.

17. The method of claim 11 wherein the sample is analyzed for a biomarker anti-β-glucan antibody using an enzyme-linked immunosorbent assay (ELISA).

18. The method of claim 11 wherein the endpoint comprises clinical outcomes, binding to immune cells, activation of complement components, modulation of immune cell surface marker expression, or induction of cytokines.

19. The method of claim 11 wherein the predetermined cutoff value is about 20 µg/ml anti-β-glucan IgG.

* * * * *